(12) United States Patent
Johnson et al.

(10) Patent No.: US 10,144,954 B2
(45) Date of Patent: Dec. 4, 2018

(54) METHODS FOR GENERATING STABILIZED LYOPHILIZED MATERIALS

(71) Applicant: LUMINEX CORPORATION, Austin, TX (US)

(72) Inventors: Scott Johnson, Austin, TX (US); Jen Dillman, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 0 days.

(21) Appl. No.: 15/654,942

(22) Filed: Jul. 20, 2017

(65) Prior Publication Data

US 2017/0321254 A1 Nov. 9, 2017

Related U.S. Application Data

(63) Continuation of application No. 14/740,365, filed on Jun. 16, 2015, now Pat. No. 9,738,923.

(60) Provisional application No. 62/013,695, filed on Jun. 18, 2014.

(51) Int. Cl.
*C12Q 1/6848* (2018.01)
*C12Q 1/6806* (2018.01)

(52) U.S. Cl.
CPC ......... *C12Q 1/6806* (2013.01); *C12Q 1/6848* (2013.01)

(58) Field of Classification Search
CPC .......................... C12Q 1/6806; C12Q 1/6848
See application file for complete search history.

(56) References Cited

U.S. PATENT DOCUMENTS

| | | | |
|---|---|---|---|
| 5,413,924 | A | 5/1995 | Kosak et al. |
| 5,550,044 | A | 8/1996 | Kosak et al. |
| 5,556,771 | A | 9/1996 | Shen et al. |
| 5,599,660 | A | 2/1997 | Ramanujam et al. |
| 5,614,387 | A | 3/1997 | Shen et al. |
| 5,834,254 | A | 11/1998 | Shen et al. |
| 2003/0180352 | A1 | 9/2003 | Patel et al. |
| 2005/0069898 | A1 | 3/2005 | Moon et al. |
| 2007/0259348 | A1 | 11/2007 | Phadke et al. |
| 2008/0070281 | A1 | 3/2008 | White et al. |
| 2008/0182338 | A1 | 7/2008 | Abraham-Fuchs et al. |
| 2010/0136542 | A1 | 6/2010 | Lee et al. |
| 2011/0059547 | A1 | 3/2011 | Dehal et al. |

FOREIGN PATENT DOCUMENTS

| | | |
|---|---|---|
| EP | 0 726 310 | 7/2003 |
| EP | 1 629 118 | 9/2006 |
| EP | 0 917 568 | 3/2007 |
| WO | WO 93/00807 | 1/1993 |
| WO | WO 94/17106 | 8/1994 |
| WO | WO 2011/069528 | 6/2011 |
| WO | WO 2013/006312 | 1/2013 |

OTHER PUBLICATIONS

Extended European Search Report issued in corresponding European Application No. 15809313.8, dated Feb. 19, 2018.
Kaijalainen et al., "An alternative hot start technique for PCR in small volumes using beads of wax-embedded reaction components dried in trehalose," *Nucl. Acid Res.*, 21(12):2959-2960, 1993.
Cloran and McMahon, "Use of coating to protect lyophilized *Bacillus popilliae* from moisture," *Applied Microbiology*, 26:502-504, 1973.
Crowe, et al., "Stabilization of dry phospholipid bilayers and proteins by sugars," *Biochem.*, 242:1-10, 1987.
Crowe, et al., "The trehalose myth revisited: introduction to a symposium on stabilization of cells in the dry state," *Cryobiology*, 43:89-105, 2001.
International Search Report and Written Opinion, issued in PCT/US2015/035921, dated Nov. 5, 2015.
Invitation to Pay Additional Fees, issued in PCT/US2015/035921, dated Aug. 24, 2015.
Office Communication, issued in U.S. Appl. No. 14/740,365, dated Sep. 8, 2016.
Office Communication, issued in U.S. Appl. No. 14/740,365, dated Feb. 10, 2017.
Raja, et al., "Increased sensitivity of one-tube, quantitative RT-PCR,"*BioTechniques*, 29:702-706, 2000.

*Primary Examiner* — Jezia Riley
(74) *Attorney, Agent, or Firm* — Parker Highlander PLLC

(57) ABSTRACT

Lyophilized biological reagents, such as enzymes (e.g., PCR reagents) and antibodies, are provided that include a wax component. Thus, in some aspects, a method is provided for storing a biological reagent comprising formulating the reagent into a lyophilized composition including a wax component. Methods for using such lyophilized reagents are likewise provided.

21 Claims, 23 Drawing Sheets

With wax   No wax. Exposed to humidity

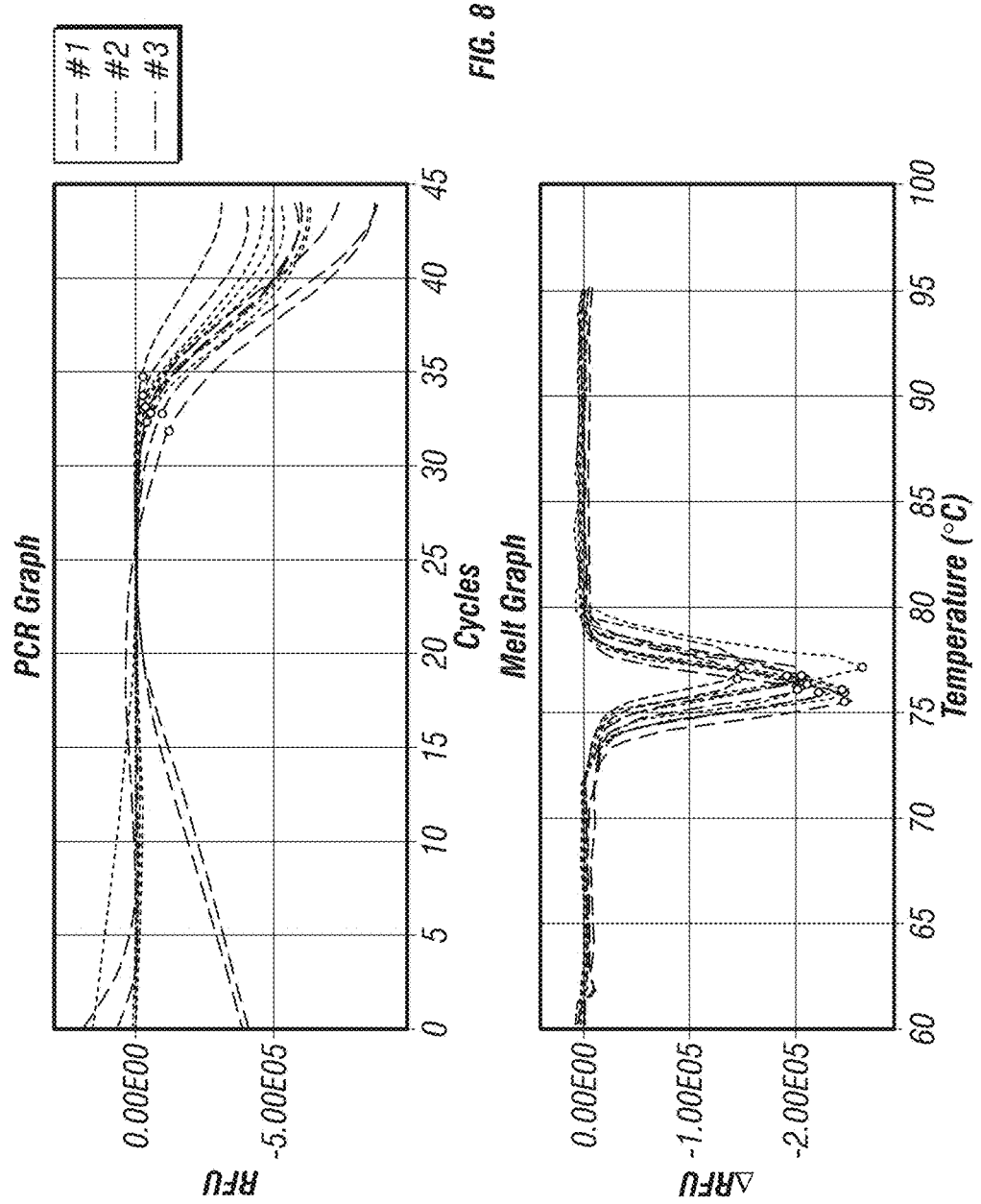

FIG. 10

METHODS FOR GENERATING STABILIZED LYOPHILIZED MATERIALS

This application is a continuation of U.S. patent application Ser. No. 14/740,365, filed Jun. 16, 2015, which claims the benefit of U.S. Provisional Patent Application No. 62/013,695, filed Jun. 18, 2014, the entirety of which is incorporated herein by reference.

BACKGROUND OF THE INVENTION

1. Field of the Invention

The present invention relates generally to the field of molecular biology, immunology, recombinant DNA technology, and nucleic acid amplification. More particularly, it concerns lyophilized biological reagents that include a wax component and the use of such reagents.

2. Description of Related Art

Most biological reagents are inherently unstable at ambient temperatures. Lyophilization (freeze-drying) is one approach that can be used to stabilize biological reagents such that they can be stored for an extended period of time at room temperature. Excipients, such as sugars, proteins, polymers, buffers, and surfactants, can be added to stabilize the lyophilized biomolecule. For example, Crowe, et al. describes the stabilization of dry phospholipid bilayers and proteins by sugars (*Biochem. J.* 242: 1-10 (1987)), and also reviews the understanding of the mechanisms of trehalose stabilization of cells in "The trehalose myth revisited: Introduction to a symposium on stabilization of cells in the dry state" Cryobiology 43, 89-105 (2001). Lyophilization of biological reagents results in generation of material with very low moisture content (<5%), and the functionality of the lyophilized material is compromised if it is not stored dry. Achieving dry storage conditions can involve the use of secondary storage containers, vacuum sealing, or low-humidity storage facilities or chambers. However, these storage mechanisms can be cumbersome. Accordingly, there is a need for stabilized, lyophilized biological compositions that can be stored at ambient temperature and humidity.

SUMMARY OF THE INVENTION

In a first embodiment there is provided a composition of stabilized lyophilized biological reagents comprising a lyophilized pellet comprising at least one biological reagent, said pellet being coated or impregnated with a wax component. It was surprisingly found that the wax does not adversely affect the lyophilized pellet, but rather protects the lyophilized pellet by reducing or preventing moisture absorption by the lyophilized pellet. Moreover, for certain application such as PCR, the wax provides an additional benefit by serving as an evaporation barrier after it has been melted away from the lyophilized pellet and formed a layer on top of the aqueous PCR solution.

In certain aspects, a lyophilized pellet of the embodiments comprises two three four or more different biological reagents. In certain aspects a lyophilized pellet of the embodiments is provided in a container, such as tube or a well. The tube may be, for example, a PCR tube. The well may be, for example, a well of a multi-well plate. Preferably the tube or well is composed of a substantially non-reactive material such as a plastic. In still further aspects, a plate is provided comprising a plurality of lyophilized pellets of the embodiments, such that each pellet is disposed in a separate well of the plate.

Thus, some aspects of the embodiments concern wax components that coat or are impregnated in a lyophilized pellet of the embodiments. In some aspects, the wax component can comprise an animal, plant, mineral or petroleum derived wax, or mixtures of such waxes. In still further aspects, the wax can comprise a purified wax or a synthetic wax (e.g., polyethylene or chemically-modified waxes). For example, a composition of the embodiments may comprise an animal wax such as beeswax, Chinese wax, or shellac. In further aspects, composition comprises a plant derived wax such as bayberry wax, candelilla wax, carnauba wax, castor wax, esparto wax, japan wax, jojoba wax, ouricury wax, rice bran wax, soy wax or tallow tree wax. In still further aspects, the wax component can comprise a mineral wax (e.g., ceresin wax, or ozocerite) or petroleum wax (e.g., paraffin, microcrystalline wax, docosane, silicone wax, Chill-out™ wax, or petroleum jelly). A skilled artisan will recognize that a wax can be comprised of a plurality of different hydrocarbon or substituted hydrocarbon molecules or may be composed essentially of a single species of molecule. In certain preferred embodiments, the wax is a solid under storage conditions (e.g., at room temperature) and a liquid at at least one temperature during the relevant biological/chemical reaction. For example, if the lyophilized pellet comprises reagents for a reverse transcription reaction at 50° C., the wax would preferably have a melting temperature below 50° C. but above the temperature at which the lyophilized pellet is stored. In this manner the wax melts away from the lyophilized pellet allowing the reagents to rehydrate when it is heated to the reaction temperature. Waxes with higher melting temperatures could be used, but would need to be initially heated above the reaction temperature to separate the wax from the lyophilized pellet before proceeding with the reaction at the lower temperature.

In further aspects, the wax component (that coats or impregnates a lyophilized pellet of the embodiments) is composed of a mixture of at least two, three or four different waxes or at least one, two or three waxes and at least one, two or three oils. In some aspects, the wax component is composed of docosane and polydimethylsiloxane (PDMS) oil. For example, in some aspects, a wax component can include about 10%, 15%, 20%, 25%, 30%, 35%, 40%, 45% or 50% docosane by volume, or any range derivable therein, and the balance of PDMS oil (i.e., 50%, 55%, 60%, 65%, 70%, 75%, 80%, 85% or 90% PDMS oil, or any range derivable therein). Optionally, a wax component may comprise docosane, paraffin and PDMS oil. For instance, in some aspects, a wax component can include about 5%, 6%, 7%, 8%, 9%, 10%, 11%, 12%, 13%, 14%, 15%, 16%, 17%, 18%, 19%, 20%, 21%, 22%, 23%, 24%, 25%, 30%, or 35% by volume docosane, or any range derivable therein; 5%, 6%, 7%, 8%, 9%, 10%, 11%, 12%, 13%, 14%, 15%, 16%, 17%, 18%, 19%, 20%, 21%, 22%, 23%, 24%, 25%, 30%, or 35% by volume paraffin, or any range derivable therein; and the balance of PDMS oil. In some aspects, the wax component comprises docosane and mineral oil. For example, in some aspects, a wax component can include about 10%, 15%, 20%, 25%, 30%, 35%, 40%, 45% or 50% docosane by volume, or any range derivable therein, and the balance of mineral oil (i.e., 50%, 55%, 60%, 65%, 70%, 75%, 80%, 85% or 90% PDMS oil, or any range derivable therein). Optionally, a wax component may comprise docosane, paraffin and mineral oil. For instance, in some aspects, a wax component can include about 5%, 6%, 7%, 8%, 9%, 10%, 11%, 12%, 13%, 14%, 15%, 16%, 17%, 18%, 19%, 20%, 21%, 22%, 23%, 24%, 25%, 30%, or 35% by volume docosane, or any range derivable therein; 5%, 6%, 7%, 8%, 9%, 10%, 11%, 12%, 13%, 14%, 15%, 16%, 17%, 18%, 19%, 20%, 21%, 22%, 23%, 24%, 25%, 30%, or 35% by volume paraffin, or any range derivable therein; and the balance of mineral oil.

Certain wax components for use according to the embodiments include, but are not limited to (in percent by volume), (1) 25-35% docosane and 65-75% PDMS oil; (2) 10-45% docosane, 5-35% paraffin and 25-75% PDMS oil; or (3) 10-45% docosane, 25-55% paraffin wax and 25-40% mineral oil. Some specific wax components for use according to the embodiments include, but are not limited to (in percent by volume), (1) 30% docosane and 70% PDMS oil; (2) 15% docosane, 15% paraffin and 70% PDMS oil; (3) 42% docosane, 28% paraffin and 30% PDMS oil; (4) 38.5% docosane, 31.5% paraffin and 30% PDMS oil; (5) 22.5% docosane, 7.5% paraffin and 70% PDMS oil; or (6) 20% docosane; 10% paraffin and 70% PDMS oil.

In certain aspects, a combination of waxes and oil may be used, such as paraffin wax, docosane and mineral oil. For example, paraffin wax, docosane and mineral oil can be combined at a ratio of 30:40:30 or 50:15:35. A blend of wax may be made first and then added to the lyophilized material as blended wax pellet (e.g., that is then melted by heating). A blend of wax may also be melted first and then added on top of a lyophilized material.

In further aspects, a combination of wax and oil may be used such as docosane and mineral oil. The mineral oil may, in some aspects, be added on top of the wax covered lyophilized cake. For example at least 1 µL of oil can be added on top of a wax covered lyophilized cake. In further aspects, about 5-15 µL of oil is added on top of a wax covered lyophilized cake.

In still further aspects, a two-layered wax may be used wherein one wax is solid at room temperature and the second wax is liquid at room temperature. For example, docosane wax can be added on top of a lyophilized material and then melted to generate wax impregnated lyo cake. In further aspects, a wax which is solid at less than room temperature (e.g., below 14° C.) and liquid at room temp, such as Chill-Out™ wax, is added on top of the wax impregnated lyo cake thereby allowing the liquid wax to form a seal around the lyo cake.

In some aspects, a two-layered wax may be used wherein one wax is liquid at room temperature and the second wax is solid at room temperature. For example, a wax which is solid at less than room temperature (e.g., below 14° C.) and liquid at room temp, such as Chill-Out™ wax, can be added on top of a lyophilized material to impregnate the lyo cake and then docosane wax can be added on top and melted to form a seal over the lyo cake and liquid wax.

In still further aspects, a two-layered sealing approach may be used wherein mineral oil (a higher density material than wax) is added on top of a lyophilized material so that it impregnates the lyo cake and then docosane wax (a lower density material than oil) is added on top and melted to form a seal over the lyo cake and mineral oil.

In certain embodiments, the waxes are those with a melting point of between approximately 5° C., 10° C., 15° C., 20° C., 25° C., 30° C., 35° C., or 40° C. and approximately 40° C., 45° C., 50° C., 55° C., 60° C., 65° C., 70° C., 75° C., 80° C. or 85° C. Those skilled in the art can select a wax with the appropriate melting temperature for a given application because the melting temperatures of waxes are readily available and/or readily determined. In preferred aspects, a wax for use according to the embodiments has a specific gravity less than that of the aqueous liquid. In still further aspects, the v:v ratio of the wax to the wet (i.e., prior to lyophilization) reagents or to the lyophilized pellet is between 1:5 and 5:1, 1:4 and 4:1, 1:3 and 3:1, or 1:2 and 2:1. In preferred aspects, the amount of wax component to reagent is greater than 1:4 or greater than 1:3 (e.g., greater than 1:2.5).

In still further aspects, a composition comprising a lyophilized pellet of the embodiments has a water content of less that about 10%. For example, the water content can be less than 5, 4, 3, 2 or 1%. In certain aspects, the water content is between about 0.1% and 5%.

Thus, certain aspects of the embodiments concern a biological reagent, such as a biological reagent comprised in a lyophilized pellet. In some aspects, the biological reagent is a polynucleotide such as a DNA, cDNA, or RNA (e.g., a messenger RNA (mRNA), small interfering RNA (siRNA), a micro RNA (miRNA) or a short hairpin RNA (shRNA)). In still further aspects, the biological reagent is a polypeptide. In some aspects, the biological reagent is a therapeutic reagent or an assay reagent. In a preferred aspect, a biological reagent of the embodiments is a polypeptide, such as an enzyme, a ligand or an antibody. In certain aspects, the enzyme can be a DNA methyltransferase or a nuclease such as a DNase, an RNase (e.g., RNase A, RNase H (or RNaseH-2) RNase I, RNase III, RNase L, RNase P, RNase PhyM, RNase T1, RNase T2, RNase U2 or RNase V), an exonuclease or a restriction endonuclease (e.g., a methylation sensitive restriction endonuclease). In further aspects, the enzyme is a polymerase, such a RNA polymerase, a DNA polymerase or a reverse transcriptase. In some specific examples the enzyme is a Taq polymerase or Klenow polymerase. In further examples, the biological reagent is a ligase (e.g., T4 DNA ligase).

In further aspects, of the embodiments a lyophilized pellet may comprise additional components such as a buffer, a salt, a label and/or enzymatic co-factors. For instance, in certain aspects, a lyophilized pellet of the embodiments comprises all of the components required to perform polymerase chain reaction (PCR) or reverse transcription-PCR except for a template nucleic acid molecule (and water). In some aspects, the lyophilized pellet may further comprise at least one oligonucleotide primer or at least one primer pair. In still further aspects, the lyophilized pellet comprises at least 2, 3, 4, 5, 6, 7, 8, 9 or 10 primers or primer pairs (e.g., for performing a multiplex PCR reaction). In certain aspects, the lyophilized pellet may further comprise a buffer (e.g., HEPES, MES, MOPS, TRIS or BIS-TRIS Propane) and/or nucleoside triphosphates (NTPs) (e.g., dATP, dGTP, dCTP, TTP, UTP, or a combination thereof). In certain aspects, the lyophilized pellet further comprises at least a first modified NTP, such as, for example, an isobase (e.g., iso-G or iso-C), a labeled nucleotide (e.g., dabcycl diGTP, biotin-diGTP, a fluor-labeled nucleotide or quencher-labeled nucleotide).

In further aspects, a lyophilized pellet of the embodiments comprises at least one label (i.e., a molecule that facilitates the detection of a molecule such as a nucleic acid sequence). For example, the label can be covalently attached to nucleotide or an intercalating dye. Numerous label molecules that may be used according to the embodiments are known and include, without limitation, fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3- diololate. Additional non-limiting examples of fluorophores include quantum dots, sulfonated coumarin, rhodamine, xanthene, or cyanine dyes (e.g., Alexa Fluor™ dyes), Aminomethylcoumarin (AMCA), boron-dipyrromethene (BODIPY™), Cyanine (Cy2™) or a Cyanine derivatives such as indocarbocyanine (Cy3™) or indodicarbocyanine (Cy5™), a DNA intercalating dye, 6-Carboxyfluorescein (6-FAM™), Fluorescein, Phosphoramidite (HEX™), 6-Carboxy-4',5'-Dichloro-2',7'-Dimethoxyfluorescein, Succinimidyl Ester (6-JOE™), phycobilliproteins including, but not limited to, phycoerythrin and allophycocyanin, Rhodamine derived dyes, Tetramethylrhodamine or a xanthene derivative (e.g., Oregon Green™ or Texas Red™). In some aspects, a signal amplification reagent, such as tyramide (PerkinElmer), may be used to enhance the fluorescence signal. Indirect label molecules contemplated for use according to the embodiments include, without limitation, biotin, which must be bound to another molecule such as streptavidin-phycoerythrin for detection. Pairs of labels, such as fluorescence resonance energy transfer pairs or dye-quencher pairs, may also be employed.

In some aspects, a lyophilized pellet of the embodiments further comprises a sugar (e.g., a mono-, oligo-, or polysaccharide) or a mixture of sugars. In certain aspects, the sugar is sucrose, glucose, lactose, trehalose, arabinose, pentose, ribose, xylose, galactose, hexose, idose, mannose, talose, heptose, fructose, gluconic acid, sorbitol, mannitol, methyl α-glucopyranoside, maltose, isoascorbic acid, ascorbic acid, lactone, sorbose, glucaric acid, erythrose, threose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, cyclodextrin, pustulan, chitin, agarose, keratin, chondroitin, dermatan, hyaluronic acid, alginic acid, xantham gum, or starch, or a combination of two or more of these sugars. In some particular aspects, the sugar is trehalose, dextran, mannitol, sucrose, raffinose, or a combination thereof. Exemplary combinations of sugars include, without limitation, trehalose and dextran, mannitol and dextran, or trehalose and mannitol. For example, in certain aspects, a lyophilized pellet is formed from an aqueous mixture comprising a biological reagent and about 1% to about 30% of a sugar by volume (e.g., between about 1, 2, 3, 4, 5, 6, 8, 9, 10, 11, 12, 13 or 15% sugar and about 20, 21, 22, 23, 24, 25, 26, 27, 29 or 30% sugar). In certain specific aspects, a lyophilized pellet is formed from an aqueous mixture comprising about 1-10% trehalose and/or about 1-10% dextran (e.g., about 5% trehalose and about 5% dextran).

In still further aspects, a lyophilized pellet of the embodiments further comprises a stabilizer (e.g., protein stabilizer such as bovine serum albumin (BSA) or gelatin). In certain specific aspects, a lyophilized pellet of the embodiments is formed from an aqueous mixture comprising about 0.1 to about 1.0 mg/ml of a polypeptide stabilizer such as BSA. For example, the pellet can be formed from an aqueous mixture comprising about 0.5 mg/ml of BSA.

In some aspects, the wax-stabilized lyophilized pellet may further comprise at least one solid object. The solid object can be useful in facilitating inversion of the wax and aqueous layers following the melting of the wax and/or in mixing or dispersing the lyophilized reagents into the aqueous solution following the melting of the wax. The solid object can be positioned on top of the wax-stabilized lyophilized pellet, underneath the wax-stabilized lyophilized pellet or even within the wax-stabilized lyophilized pellet. In some aspects, a the solid object may be embedded in the wax associated with the lyophilized pellet. The solid object may be, for example, a spherical (i.e., a "ball"), disk-shaped, or rod-shaped. The solid object is preferably made of, or at least coated with, a material that is inert to the reaction conditions intended for the biological reagents in the lyophilized pellet. In certain aspects, the solid object may comprise ceramic, glass, plastic (e.g., polystyrene, polyethylene, polyethene, polypropylene, neoprene, poly(tetrafluoroethylene)), or metal (e.g., stainless steel). In one embodiment, the solid object is a stainless steel object that has been passivated to remove free iron or other inclusions from its surface. Stainless steel can be passivated by, for example, by a series of acid baths, which clean free iron or other inclusions from the surface, and form a uniform natural oxide layer that protects the stainless steel from corrosion. In certain aspects, the solid object is magnetic or magnetically responsive. Where an objective of including the solid object with the wax-stabilized lyophilized pellet is to facilitate inversion of the wax and aqueous layers and/or to mix the lyophilized reagents into the aqueous solution, the solid object should be of an appropriate size to achieve these functions in view of the size and shape of the container. In certain aspects, a solid object may have a diameter or length in its longest dimension of between about 0.5 mm to about 5 mm, or between about 1 mm to about 2 mm. In some aspects, the aqueous liquid may have a specific gravity less than that of the solid object(s). In alternative aspects, the aqueous liquid may have a specific gravity greater than that of the solid object(s).

In a further embodiment, provided herein is a method of performing an enzymatic reaction comprising: (a) combining in a receptacle an aqueous liquid comprising an enzyme substrate and a wax-coated (or impregnated) lyophilized pellet according to the embodiments, wherein the wax-coated lyophilized pellet comprises an enzyme; (b) melting the wax; and (c) incubating the mixture under conditions favorable to enzymatic reaction, thereby performing preforming an enzymatic reaction. In one aspect, the method may further comprise mixing the reaction solution prior to and/or concurrent with step (c). In some cases mixing can be by agitation of the receptacle (e.g., a tube or a well), by sonication, by pipetting or by movement of the wax (e.g., by the inversion of the wax and aqueous layers upon melting of the wax) or a solid object in the receptacle (e.g., by gravity or magnetic attraction).

In still a further embodiment, provided herein is a method of performing PCR or reverse transcription PCR comprising: (a) combining in a receptacle an aqueous liquid comprising nucleic acids, and optionally one or more additional RT-PCR or PCR reagents, and a wax-coated (or impregnated) lyophilized pellet according to the embodiments, wherein the wax-coated lyophilized pellet comprises any RT-PCR or PCR reagents not provided in the aqueous liquid (with the proviso that the wax-coated lyophilized pellet contains at least one RT-PCR or PCR reagent that is not present in the aqueous liquid); (b) melting the wax; (c) optionally, performing at least one cycle of reverse transcription and (d) performing at least one cycle of PCR. In one aspect, the method may further comprise mixing the reaction solution prior to step (c) or step (d). In further aspects, the methods comprise performing a quantitative PCR reaction or quantifying the products of the PCR. In some cases mixing can be by agitation of the receptacle (e.g., a tube or a well), by sonication, by pipetting or by movement of the wax (e.g., by melting of the wax) or a solid object in the receptacle (e.g., by gravity or magnetic attraction).

In some aspects, methods of the embodiments can comprise melting a wax component of a lyophilized pellet prior to combining it with the aqueous liquid. In some aspects, the aqueous liquid may be pre-heated and the wax may be melted by combining the pre-heated aqueous liquid with the wax-coated lyophilized pellet. In further aspects, a wax component for use in the methods of the embodiments is positioned under the lyophilized pellet and comprises a specific gravity less than the aqueous liquid. Thus, in certain aspects a reaction can be mixed by melting the wax and allowing it to migrate through the aqueous liquid.

In still further aspects, a method of the embodiments further comprises measuring the homogeneity of the aqueous liquid after mixing of the reaction (e.g., by movement of a solid object in the reaction). Thus, in some aspects, one or more additional mixing steps is performed if the aqueous liquid is not determined to be sufficiently homogenous. In some specific aspects for example, measuring the homogeneity of the aqueous liquid comprises measuring the fluorescence signal of a fluorescent label in the in the aqueous liquid.

In further aspects, a method of the embodiments comprises use of a composition that comprises a solid object. In one aspect, a method may further comprise mixing the aqueous liquid (and/or a melted wax component) by inducing movement of the solid object, such as by gravity of magnetism. In certain aspects, the solid object may be a magnetic or magnetically responsive solid object and movement of the solid object may be induced by a magnet. For example, the solid object may be a stainless steel ball, disk, or rod that can be moved by a magnet. In some aspects, the solid object may be moved from the bottom of the receptacle to a position within two solid object diameters of the aqueous liquid/wax interface without the solid object contacting the aqueous liquid/wax interface. In certain aspects, a solid object is moved only one time to accomplish a mixing. In further aspects, the solid object may be moved repeatedly, such as 2, 3, 4, 5, 6, 7, 8, 9, 10, 15, 20, 30 or more times.

In still a further embodiment, a method is provided for making a composition of stabilized lyophilized biological reagents comprising: (a) lyophilizing the biological reagents (e.g., an aqueous mixture of biological reagents); and (b) forming a wax barrier that contacts and surrounds the lyophilized biological reagents to form a stabilized lyophilized pellet of biological reagents. In some aspects, the forming the wax barrier comprises adding a solid wax and then melting the wax. In further aspects, the wax is added in a molten (liquid) form. In certain aspects, forming the wax barrier may comprise combining the biological reagents and a wax prior to lyophilizing the biological reagents. Thus, in some aspects, the wax may be melted in a lyophilizer.

In some further aspects, forming the wax barrier may comprise: (a) combining the lyophilized biological reagents and a solid wax; and (b) melting the solid wax to form a liquid wax. In certain aspects, the melting of the solid wax may be performed using a heat block, oven, or microwave. In certain aspects, the melting of the solid wax may be performed under vacuum.

In some aspects, forming the wax barrier may comprise combining the lyophilized biological reagents and a liquid wax. In certain aspects, the method may further comprise heating the lyophilized biological reagents and the liquid wax. In various aspects, a method may further comprise applying a vacuum to the lyophilized biological reagents and a liquid wax. In certain aspects, the method may further comprise solidifying the wax.

In some aspects, the method may further comprise placing a solid object on top of the stabilized lyophilized biological reagents. In further aspects, the method may further comprise placing a solid object below the stabilized lyophilized biological reagents. In some aspects, the method may further comprise embedding a solid object in the wax surrounding the stabilized lyophilized biological reagents or embedding the solid object in the lyophilized pellet. In various aspects, the solid object may be a ceramic solid object, polymer solid object, glass solid object, magnetic solid object, or metal solid object.

In further specific embodiment, there is provided a method of making a composition of stabilized, lyophilized PCR or RT-PCR reagents comprising: (a) combining a solid object and one or more PCR (or RT-PCR) reagents in a receptacle; (b) lyophilizing the one or more lyophilization reagents and the one or more PCR reagents in the presence of the solid object to form lyophilized PCR reagents; (c) adding wax to the lyophilized PCR reagents; (d) melting the wax around the lyophilized PCR reagents and the solid object; and (e) re-solidifying the wax to form stabilized, lyophilized PCR reagents. In some aspects, the lyophilization reagents may comprise one or more of the sugars and stabilizers mentioned above. In particular embodiments, the lyophilization reagents may comprise one or more of trehalose, dextran, mannitol, sucrose, raffinose, or a combination thereof. In some aspects, the PCR reagents may comprise one or more of a polymerase, a reverse transcriptase, primers, or nucleotide triphosphates. In some aspects, the wax is paraffin wax, docosane, or silicone wax, plant wax, or a combination thereof.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A-B, Graphs show Ct (A) and Tm (B) values obtained by real time PCR amplification of a Mouse Hepatitis Virus (MHV) RNA and DNA. From left to right each graph shows results obtained using non-lyophilized ("wet control") PCR reagents formulated just prior to PCR cycling; PCR reagents in a lyophilized cake with no added wax component ("lyo control") or PCR reagents in a lyophilized cake that was covered with melted docosane wax ("with wax"). FIG. 5C, Graphs show amplification curve and melt curve results for real time PCR amplification of an Influenza A template nucleic acid. Curves were obtained from lyophilized PCR reagent cakes that were left untreated (A4) or covered with melted docosane wax in an amount of 10 µl (A3); 15 µl (A2); 20 µl (A1) and incubated in high humidity conditions. Curves for control reactions with non-lyophilized ("wet") PCR reagents are marked as A5 and A11. The curve for lyophilized PCR reagent cakes that were not subjected to high humidity is labeled as A6. FIG. 5D, shows lyophilized PCR reagent cakes that were exposed to high humidity conditions with or without a wax component, as indicated.

FIG. 6A shows a lyophilized PCR reagent cake over-laid with a ceramic ball (left image) and a PCR reagent cake that has been rehydrated by buffer addition, such that ceramic ball has migrated to the bottom of the tube (right image). FIG. 6B, Graph shows amplification curve and melt curve results for real time PCR amplification of a MHV template nucleic acid. Results show curves obtained from lyophilized PCR reagent cakes that were covered with melted docosane wax and over-laid with a ceramic ball (dashed curves); or with non-lyophilized ("wet") PCR reagents formulated just prior to PCR cycling (solid curves).

FIG. 7A shows a PCR reagent cake lyophilized over a stainless steel ball and covered with melted docosane wax (left image) and a PCR reagent cake that has been rehydrated by buffer addition after wax inversion (right image). FIG. 7B, Graphs show amplification curve (left panels) and melt curve (right panels) results for real time PCR amplification of a Norovirus template nucleic acid using three different fluorescence channels FAM (top panels); AP593 (center panels); and AP559 (bottom panels). Curves were obtained using (1) non-lyophilized ("wet") PCR reagents including a stainless steel ball and hand mixed (depicted as curve #1); (2) lyophilized PCR reagent cakes without a wax component and unmixed (depicted as curve #2); (3) lyophilized PCR reagent cakes without a wax component, but including a stainless steel ball that were hand mixed (depicted as curve #3); (4) lyophilized PCR reagent cakes without a wax component, but including a stainless steel ball that were magnetically mixed (depicted as curve #4); (5) lyophilized PCR reagent cakes covered with melted docosane wax and including a stainless steel ball that were not mixed (depicted as curve #5); and (6) lyophilized PCR reagent cakes covered with melted docosane wax and including a stainless steel ball that were magnetically mixed (depicted as curve #6).

FIG. 9A-C shows amplification curve (left panel) and melt curve (right panel) results for real time PCR amplification of a Norovirus RNA. Lyophilized PCR reagent cake over-laid with a 25 µL docosane wax (9A) or docosane wax overlay followed by 15 µL of Chill Out™ wax (9B) or docosane wax overlay followed by 15 µL of mineral oil (9C) were stored in a 80% Relative Humidity chamber (dashed lines) or in a sealed, dry chamber (solid lines) Results show that the docosane, or docsane overlaid with chill out wax or docosane overlaid with mineral oil provides an effective vapor barrier.

FIG. 10: Graph show the results of real-time PCR amplification of a Norovirus RNA. Lyophilized PCR reagent cake over-laid with a 30 µL docosane wax, or docosane wax overlay followed by 15 µL of mineral oil, or lyophilized PCR reagent cake over-laid with a 30 µL blend of waxes (Paraffin wax:Docosane wax:mineral oil in the ratio of 30:40:30) or lyophilized PCR reagent cake over-laid with 30 µL Paraffin wax stored in dry box (T1 CTRL), or stored in ambient environment (T1 Ambient) of stored in a 80% Relative Humidity chamber (T1 80%). Lyophilized PCR reagent cake over-laid with a 30 µL docosane wax and stored in a 80% Relative Humidity chamber did not generate any PCR amplification result.

DESCRIPTION OF ILLUSTRATIVE EMBODIMENTS

Figure 1:
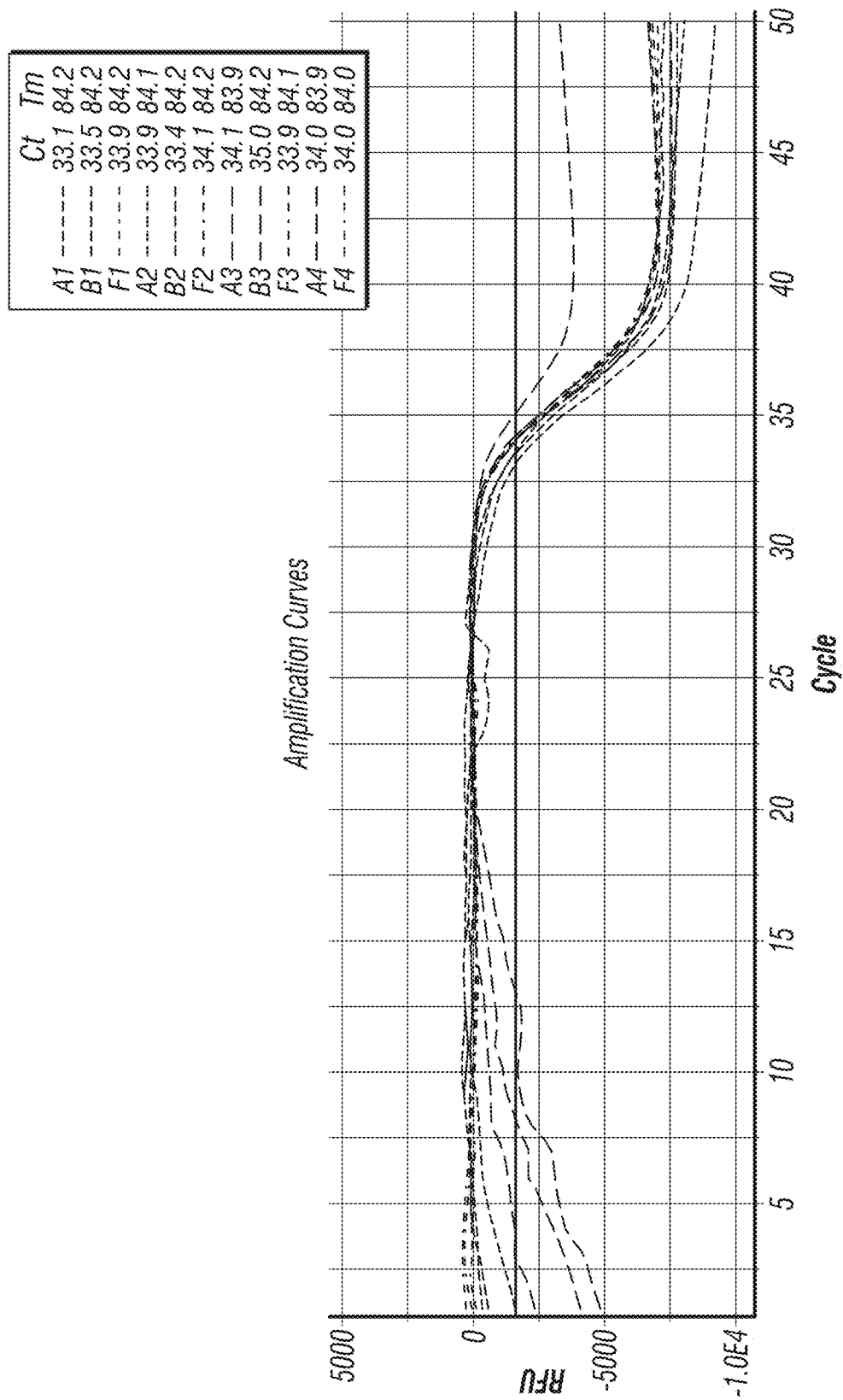
FIG. 1: Graphs show amplification curve and melt curve results for real time PCR amplification of an Influenza A template nucleic acid. Curves were obtained using lyophilized PCR reagent cakes that were covered with docosane wax (curves indicted as A1; B1; A2; and B2); Chill-Out™ wax (A3; B3; and A4); or with no added wax component (curves indicted as F1; F2; F3; and F4).
Figure 1:
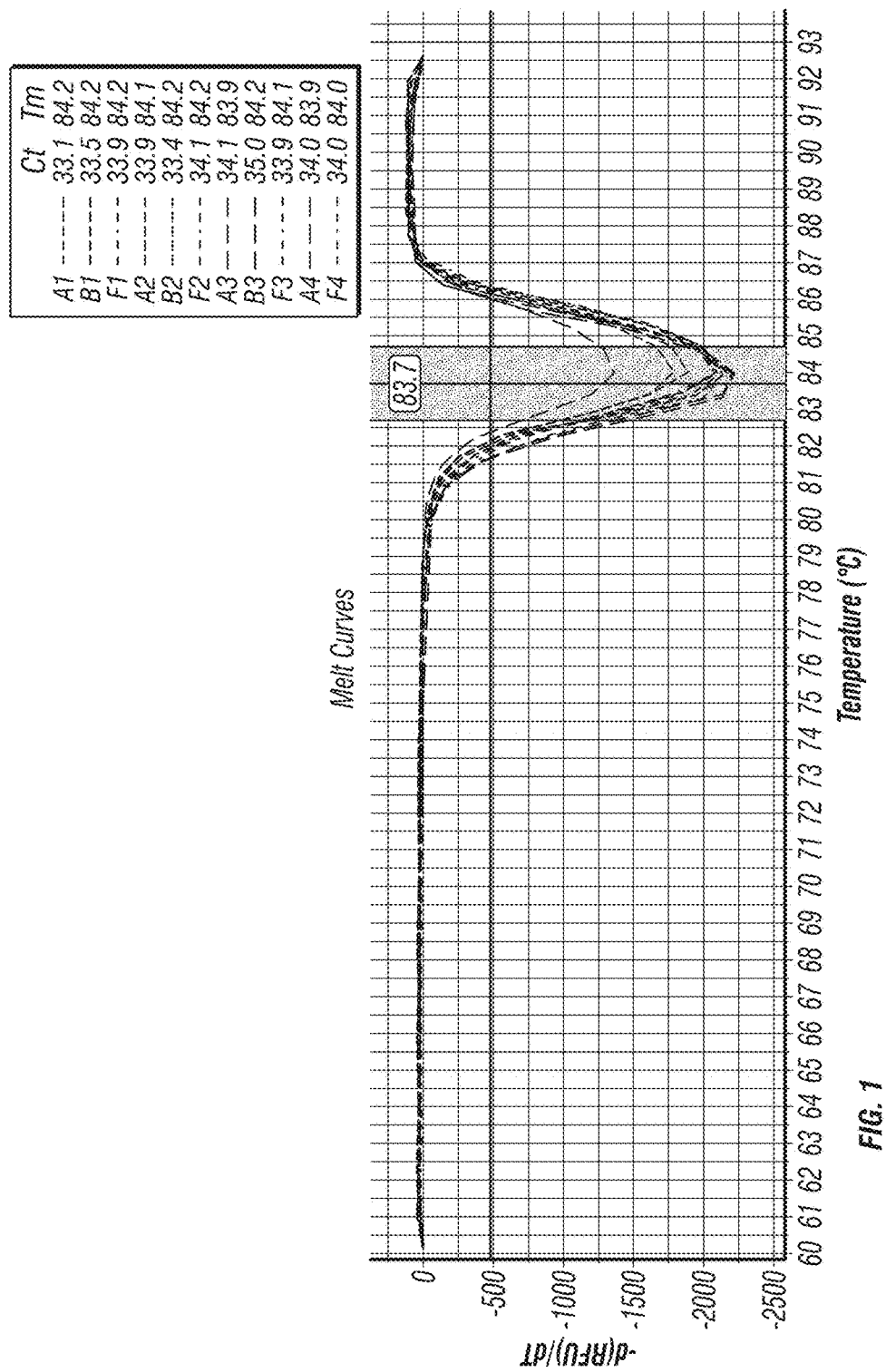

Biological reagents are inherently unstable at ambient temperatures and are often stabilized with sugars via lyophilization. Lyophilizing any biological material (nucleic acid/proteins/lipid/carbohydrate) results in generation of lyophilized cakes or pellets that need to be protected from moisture. Embodiments of the present invention offer a solution to keep biological molecules protected from environmental moisture. Wax provides a barrier to prevent or inhibit moisture from accessing the lyophilized biological material, once the lyophilized material is removed from the lyophilizer. This can be achieved by melting wax over a lyophilized cake after removal from the lyophilizer using, for example, a heat block or oven or vacuum oven, or by apply the wax in a liquid form to the lyophilized cake. Alternatively, lyophilizing the biological reagent in presence of wax and melting the wax within the lyophilizer upon completion of lyophilization cycle also allows for generation of lyophilized cakes that are protected from atmospheric moisture. The process of lyophilization involves removal of water from a frozen biological material/reagent under vacuum via sublimation. Sugars and stabilizers can be added to aid in retaining the structure of the proteins and other biological material so that the functional activities of the biological material are not compromised.

Thus, in one aspect, the present disclosure provides a method for increasing the stability of lyophilized reagents, by contacting lyophilized material with wax. For example, a wax can be added in a manner so that the wax forms a layer around the lyophilized material or such that the lyophilized material becomes impregnated with the wax component. Preferably, the wax solidifies at ambient temperature and forms a barrier around the lyophilized material preventing any moisture exchange with the environment. Importantly, studies presented here demonstrate that such lyophilized wax compositions are able to maintain biological activity of the components in the formulation. In particular, studies demonstrate that reagents used for PCR can be reliably stored in a wax-lyophilized form and that enzymatic activity of, for example, a polymerase is not only maintained but remains sufficiently active to provide quantitative amplification of a target nucleic acid. Thus, the studies indicate that proteins even enzymes such a polymerases, which are sensitive to contaminants in a reaction, can be stored and remain highly active in a lyophilized wax formulation. Accordingly, lyophilized formulations including a wax component can be used to store a wide range biologically active molecules, such as enzymes and antibodies while effectively maintaining the biological activity of the molecules.

In certain specific aspects, wax formulations of the embodiments can comprise reagents for performing PCR cycling. Such formulation can be generated by either adding the wax a part of the lyophilization process or by covering a lyophilized reagent cake with a wax (e.g., a molten wax) after lyophilization. In this aspect, following storage the wax is melted prior to or concurrent with PCR cycling and the lyophilized reagents come in contact with the added target molecule that is to be amplified. Thus, in some cases, the wax is also used as a vapor barrier during PCR, to prevent evaporation from the reaction. Furthermore, after PCR cycling, the wax can solidify and create a full or partial barrier to potential amplicon contamination.

I. Reagents for Formulation in Lyophilized Compositions

In some aspects, lyophilized pellets are provided comprising a biological reagent and a wax component (e.g., coating the pellet), such as a low-temperature melting wax. As used herein the term "lyophilized pellet" or "lyophilized cake" are used interchangeably and refer to a mass of material that has substantially reduced in water content, e.g., to less than about 5% water. Such cakes or pellets can be of any shape or size.

As used herein a low-temperature melting wax is a wax material having a melting point of approximately 25° C. to 75° C. The wax material may have a melting point slightly higher than normal human body temperature, i.e., approximately 37° C. to 45° C. Example wax materials include the straight-chain alkanes, such as N-docosane, N-eicosane, and mixtures thereof. N-docosane and N-eicosane have melting points of approximately 42-45° C. and 36-38° C., respectively. Other exemplary wax materials are paraffin wax and silicone wax. Silicone waxes behave like typical hydrocarbon waxes in that they undergo a phase transition from a solid to a viscous liquid over some well-defined temperature range, usually slightly above room temperature.

In some aspects, a wax-covered pellet of the invention may either contain a solid object (e.g., a ball, disk, or rod) or there may be a solid object placed on top of the pellet. Such a solid object may, for example, be a ceramic ball, magnetic ball, metal ball (e.g., stainless steel), or glass ball. The ball may, for example, have a diameter between approximately 0.5 mm and approximately 10 mm.

Many sugars stabilize biomolecules in solution and afford protection to isolated cells and biomolecules. Therefore, in some aspects, a wax-covered pellet of the invention may comprise sugars, for example, saccharides and polyols (e.g., trehalose, dextran, mannitol, sucrose, and raffinose) in order to improve the stability of the biomolecule and prolong shelf life. Sugars may be used in combinations, such as, for example, trehalose and dextran, mannitol and dextran, or trehalose and mannitol. Without being bound by theory, there are two main theories on the mechanism of the stabilizing action of sugars: 1) the sugar excipients serve to dilute proteins in the solid state, thereby decreasing protein-protein interactions and preventing molecular degradation, such as aggregation, and 2) the sugar excipients provide a glassy matrix wherein protein mobility and hence reactivity are minimized. In both of these mechanisms, it is believed to be important that the sugar remains in the amorphous, protein-contacting phase. Various environmental factors, such as increased temperature and moisture, can induce sugar crystallization.

In addition, inert proteins may also be used to stabilize biomolecules. An inert protein refers to a naturally occurring or synthetic peptide or polypeptide, or mixtures thereof, that does not interfere with enzyme activity. Examples not limiting the scope of the present invention are globulin, albumin (e.g., bovine serum albumin), collagen and derivatives thereof. The protein is preferentially present at a concentration of over 0.01 mg/ml, over 0.05 mg/ml and over 0.1 mg/ml. Preferably, the concentration is not over 2 mg/ml. In a preferred embodiment, the inert protein is bovine serum albumin (BSA) as well derivatives and fragments thereof. Fragments thereof have more than 50% of the length of naturally occurring BSA, more than 60% of the length of naturally occurring BSA, more than 70% of the length of naturally occurring BSA, more than 80% of the length of naturally occurring BSA, more than 90% of the length of naturally occurring BSA, and most preferentially more than 95% of the length of naturally occurring BSA.

In some aspects, a wax-covered pellet of the invention may contain one or more buffer suitable for use with the lyophilized biomolecule. Such buffers include, for example, bis-tris propane (BTP) and Tris.

In various aspects, a wax-covered pellet of the embodiments will contain at least one biological reagent, such a polypeptide. Such biological reagents include, for example, an enzyme (e.g., DNA polymerase, Taq polymerase, reverse transcriptase, RNA polymerase, Klenow polymerase, ligase, RNase H-2), nucleic acid molecules (e.g., primers or probes), and antibodies. In some aspects, various components of an amplification mixture for PCR may be present. In further aspects, components required complete a nucleic acid hybridization reaction can be comprised in a lyophilized pellet of the embodiments. In still further aspects, components required complete binding hybridization of proteins or protein-protein interactions are comprised in a pellet.

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions ($Mg^{2+}$); and monovalent cation potassium ions.

Amplification mixtures may include natural nucleotides (including A, C, G, T, and U) and non-natural or non-standard nucleotides (e.g., including isoC, isoG, labeled nucleotides, dabcyl diGTP, biotin-diGTP). DNA and RNA oligonucleotides include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases hybridize to form purine-pyrimidine base pairs, where G pairs with C and A pairs with T or U. These pairing rules facilitate specific hybridization of an oligonucleotide with a complementary oligonucleotide.

As used herein "nucleic acid" means either DNA or RNA, single-stranded or double-stranded, and any chemical modifications thereof. Modifications include, but are not limited to, those which provide other chemical groups that incorporate additional charge, polarizability, hydrogen bonding or electrostatic interaction to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, and methylations. Accordingly, the nucleic acids described herein include not only the standard bases adenine (A), cytosine (C), guanine (G), thymine (T), and uracil (U) but also non-standard or non-natural nucleotides. Non-standard or non-natural nucleotides also include bases that form non-natural hydrogen-bonding base pairs (e.g., isobases). By "non-standard nucleotide" or "non-natural nucleotide" it is meant a base other than A, G, C, T, or U that is susceptible to incorporation into an oligonucleotide and that is capable of base-pairing by hydrogen bonding, or by hydrophobic, entropic, or van der Waals interactions, with a complementary non-standard or non-natural nucleotide to form a base pair. Some examples include the base pair combinations of iso-C/iso-G, K/X, K/P, H/J, and M/N, as illustrated in U.S. Pat. No. 6,037,120, incorporated herein by reference. Other non-standard nucleotides for use in oligonucleotides include, for example, naphthalene, phenanthrene, and pyrene derivatives as discussed, for example, in Ren, et al., J. Am. Chem. Soc. 1996, 118:1671 and McMinn et al., J. Am. Chem. Soc. 1999, 121:11585, both of which are incorporated herein by reference. These bases do not utilize hydrogen bonding for stabilization, but instead rely on hydrophobic or van der Waals interactions to form base pairs.

In some aspects, non-natural bases that differ from the naturally occurring bases (A, T, C, G, and U) in their hydrogen bonding pattern may be incorporated into the primers and probes described herein. One example are the isoC and isoG bases that hydrogen bond with each other, but not with natural bases. The incorporation of these non-natural bases in primers and/or probes is useful in reducing non-specific hybridization. Methods of using such non-natural bases to assay target nucleic acids are disclosed in U.S. Pat. Nos. 6,977,161 and 7,422,850, which are incorporated herein by reference. In one aspect, at least one of the two target-specific primers used to amplify the target nucleic acid includes at least 1, 2, 3, or 4 non-natural bases, and the complementary non-natural base is included in the amplification reaction, such that the non-natural base(s) is included in the amplification product.

A primer is a nucleic acid that is capable of priming the synthesis of a nascent nucleic acid in a template-dependent process. A target-specific primer refers to a primer that has been designed to prime the synthesis of a particular target nucleic acid. A primer pair refers to two primers, commonly known as a forward primer and a reverse primer, which are designed to amplify a target sequence between the binding sites of the two primers on a template nucleic acid molecule. In certain embodiments, the primer has a target-specific sequence that is between 10-40, 15-30, or 18-26 nucleotides in length.

A probe is a nucleic acid that is capable of hybridizing to a complementary nucleic acid. A target-specific probe refers to a probe that has been designed to hybridize to a particular target nucleic acid. Probes present in the reaction may comprise a blocked 3' hydroxyl group to prevent extension of the probes by the polymerase. The 3' hydroxyl group may be blocked with, for example, a phosphate group, a 3' inverted dT, a ribonucleotide, or a label. High stringency hybridization conditions may be selected that will only allow hybridization between sequences that are completely complementary.

As used herein, "labels" are chemical or biochemical moieties useful for labeling a nucleic acid. "Labels" include fluorescent agents, chemiluminescent agents, chromogenic agents, quenching agents, radionuclides, enzymes, substrates, cofactors, scintillation agents, inhibitors, magnetic particles, and other moieties known in the art. "Labels" are capable of generating a measurable signal and may be covalently or noncovalently joined to an oligonucleotide. Numerous labels that may be used to label nucleic acids are known, including but not limited to fluorophores, chromophores, and radiophores. Non-limiting examples of fluorophores include, a red fluorescent squarine dye such as 2,4-Bis[1,3,3-trimethyl-2-indolinylidenemethyl] cyclobutenediylium-1,3-dioxolate, an infrared dye such as 2,4 Bis [3,3-dimethyl-2-(1H-benz[e]indolinylidenemethyl)] cyclobutenediylium-1,3-dioxolate, or an orange fluorescent squarine dye such as 2,4-Bis [3,5-dimethyl-2-pyrrolyl] cyclobutenediylium-1,3-diololate.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Fluorescent dyes or fluorophores may include derivatives that have been modified to facilitate conjugation to another reactive molecule. As such, fluorescent dyes or fluorophores may include amine-reactive derivatives, such as isothiocyanate derivatives and/or succinimidyl ester derivatives of the fluorophore.

A quencher as used herein is a moiety that absorbs and thereby decreases the apparent intensity of a fluorescence moiety when in close proximity to a fluorescence moiety. In some aspects, a quencher for use according to the embodiments emits the absorbed fluorescence in different spectrum. Thus, in some aspects, a detection method of the embodiments employs a filter that to reduce or remove fluorescence emitted by a quencher. In certain aspects, a quencher is a dark quencher with no native fluorescence and therefore do not occupy an emission bandwidth. Such a dark quencher is a substance that absorbs excitation energy from a fluorophore and dissipates the energy as heat. Examples of dark quenchers include, but are not limited to, Dabcyl, Black Hole Quenchers, Qxl quenchers, Iowa black FQ, Iowa black RQ, and IRDye QC-1.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the trade name "BHQ" (e.g., BHQ-0, BHQ-1, BHQ-2, and BHQ-3, Biosearch Technologies, Novato, Calif.). Dark quenchers also may include quenchers sold under the trade name "QXL™" (Anaspec, San Jose, Calif.). Dark quenchers also may include DNP-type non-fluorophores that include a 2,4-dinitrophenyl group.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Use of Docosane and Chill-Out™ Wax as Barriers to the Lyophilized Reagent Cake

Studies were undertaken to test whether lyophilized cakes comprising reagents for performing PCR could be protected by wax sealing, while still maintaining the ability to achieve robust and quantitative PCR. Lyophilized cakes contained all of the reagents for real-time PCR amplification and detection of an Influenza A target sequence. These reagents were dried-down together in a 50 µL cake. These cakes were then treated with two different waxes. In one case, 60 µL of docosane wax was pipetted on top of the lyophilized cakes and allowed to solidify at room temperature. In a second test case 60 µL of Chill-Out™ wax (Bio-Rad Laboratories, Inc.) was pipetted on top of the lyophilized cakes and placed in a cold plate to solidify. Chill-Out™ wax added in this manner absorbs into the lyophilized cake and remains solid as long as the cakes are kept below 10° C.

Upon rehydration and template addition, the docosane and Chill-Out™ wax reagent cakes were compared in a PCR assay to "control" lyophilized cakes containing no wax (but that included a mineral oil vapor barrier during PCR). All material was tested side by side on the thermocycler apparatus using RT-PCR (Reverse transcriptase at 50° C. for 15 min followed by a denaturation step of 2 min at 95° C. followed by 50 cycles of PCR (95° C./5 sec-58° C./10 sec-72° C.-30 sec) and a melt step from 60° C. to 95° C.). Results indicate that the Ct and Tm values and melt deflection are comparable across docosane or Chill-Out™ wax and "no wax lyo pellet" (see, e.g., FIG. 1), which indicated that a wax protective layer (wax impregnated) reagent cake maintains robust enzymatic activity and is able to achieve comparable quantitative characteristics as compared to control reagent cakes.

Example 2

Use of Paraffin Wax as Vapor Barrier to the Lyophilized Cake

Lyophilized reagent cakes (25 µL) were prepared in snap cap tubes that comprise real-time PCR reagents and primers for Influenza A amplification. Unless otherwise detailed, lyophilized reagent cakes produced according to the instant examples were produced from a starting wet reagent volume of 25 µL and included 5% trehalose (w/v), 5% dextran (w/v), and 0.5 mg/mL BSA. Paraffin wax was added to a subset of the tubes by melting a 20 µL paraffin wax pellet over the lyophilized cake. The wax was melted on a heat block at 70° C. for 1.5 minutes.

Figure 2:
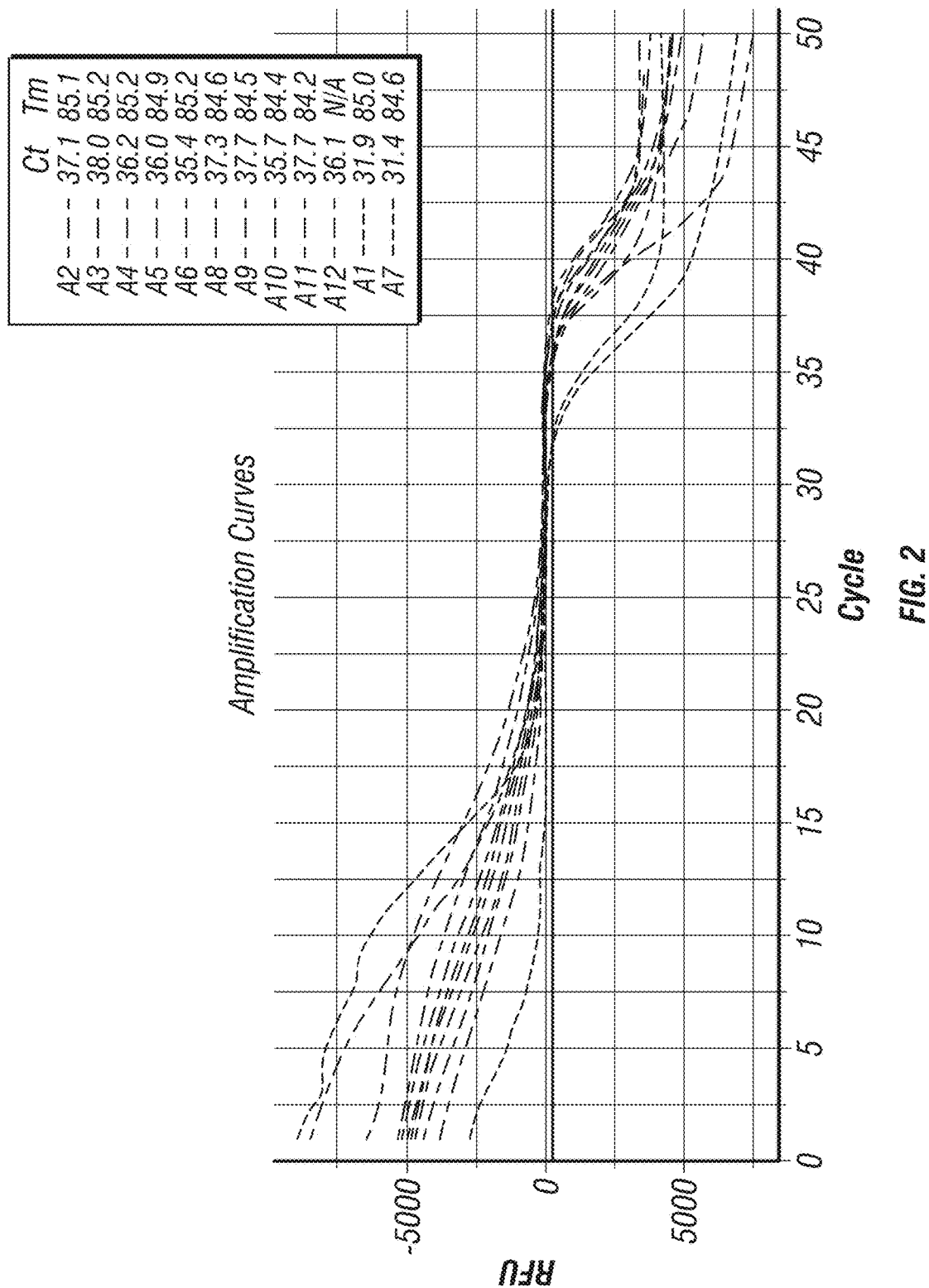
FIG. 2: Graphs show amplification curve and melt curve results for real time PCR amplification of an Influenza A template nucleic acid. Curves were obtained using lyophilized PCR reagent cakes that were covered with melted paraffin wax (curves indicted as A2; A3; A4; A5; A6; A8; A9; A10; A11; and A12); or with non-lyophilized ("wet") PCR reagents formulated just prior to PCR cycling (curves indicted as A1; and A7).
Figure 2:
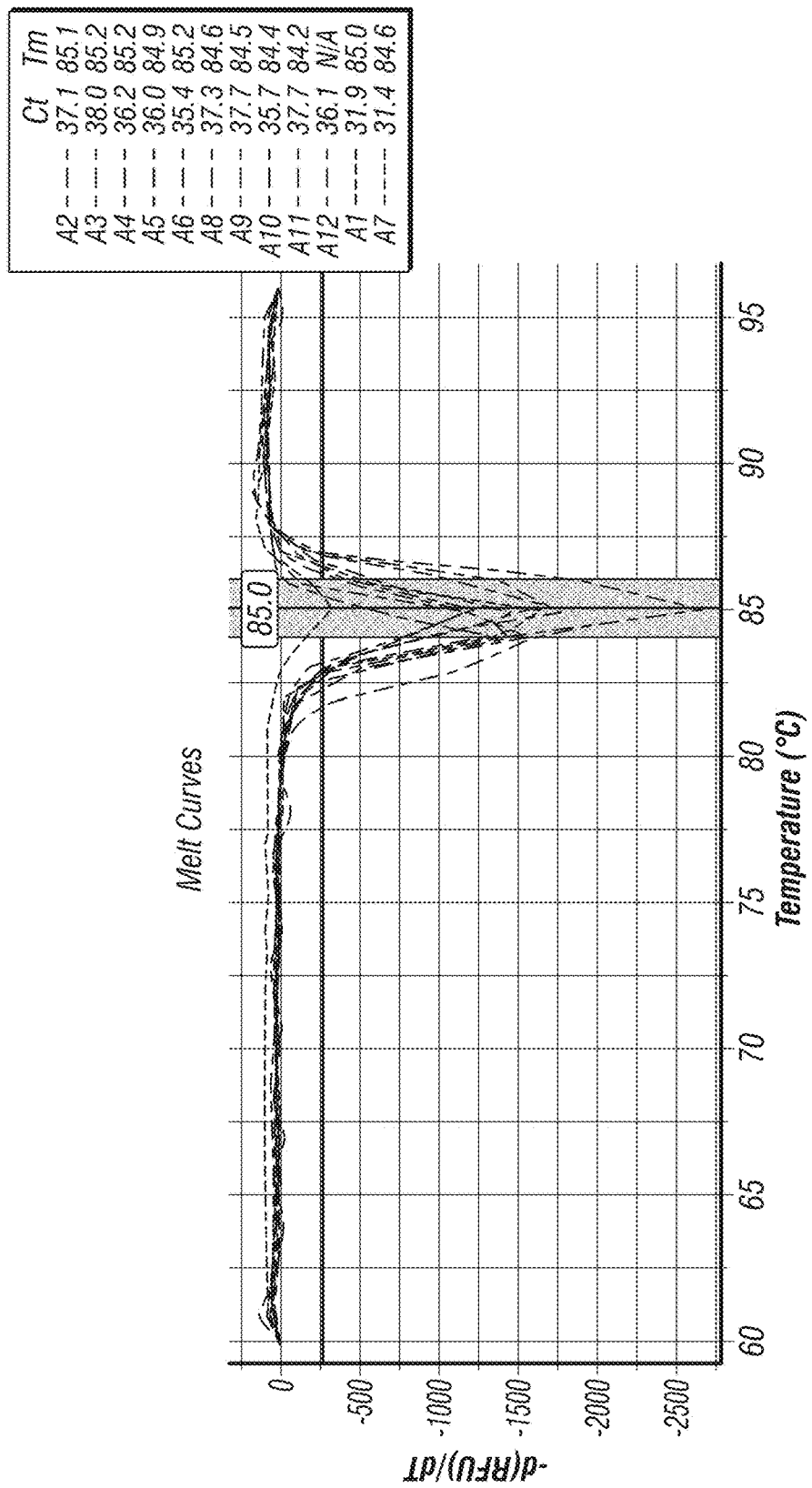
Figure 3:
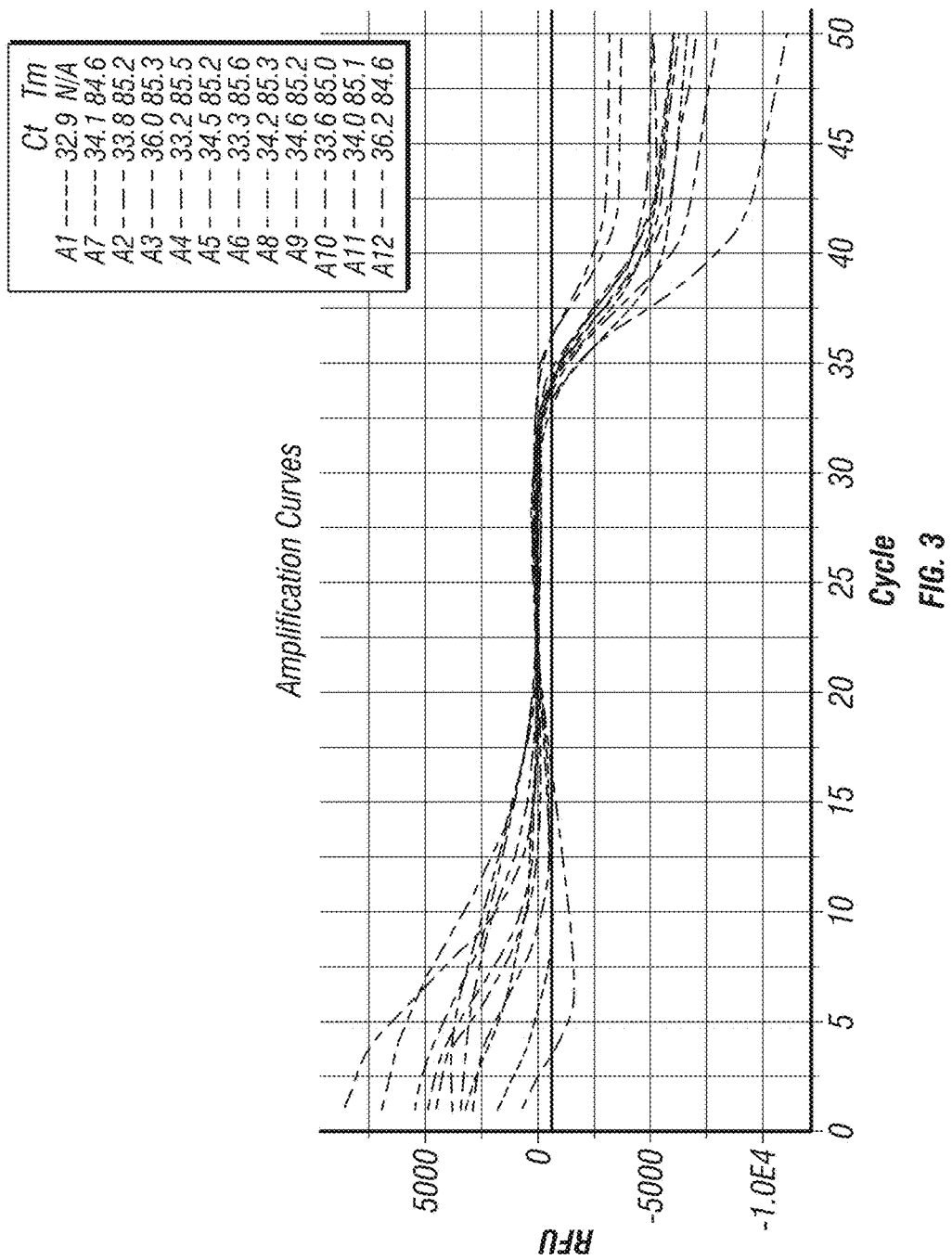
FIG. 3: Graphs show amplification curve and melt curve results for real time PCR amplification of an Influenza A template nucleic acid. Curves were obtained using lyophilized PCR reagent cakes that were over-laid with a docosane wax pellet (curves indicted as A2; A3; A4; A5; A6; A8; A9; A10; A11; and A12); or with non-lyophilized ("wet") PCR reagents formulated just prior to PCR cycling (curves indicted as A1 and A7).
Figure 3:
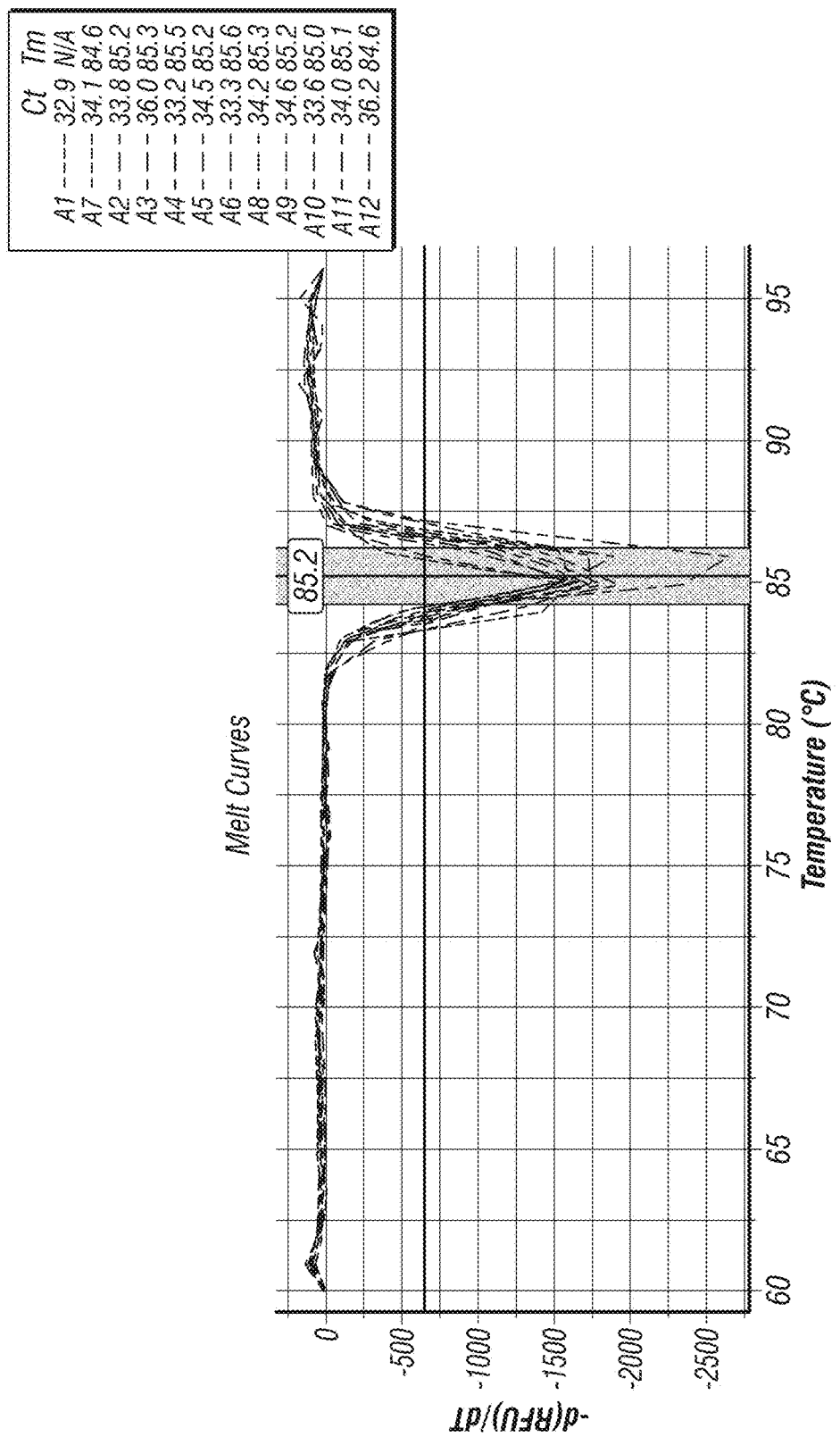
Figure 4:
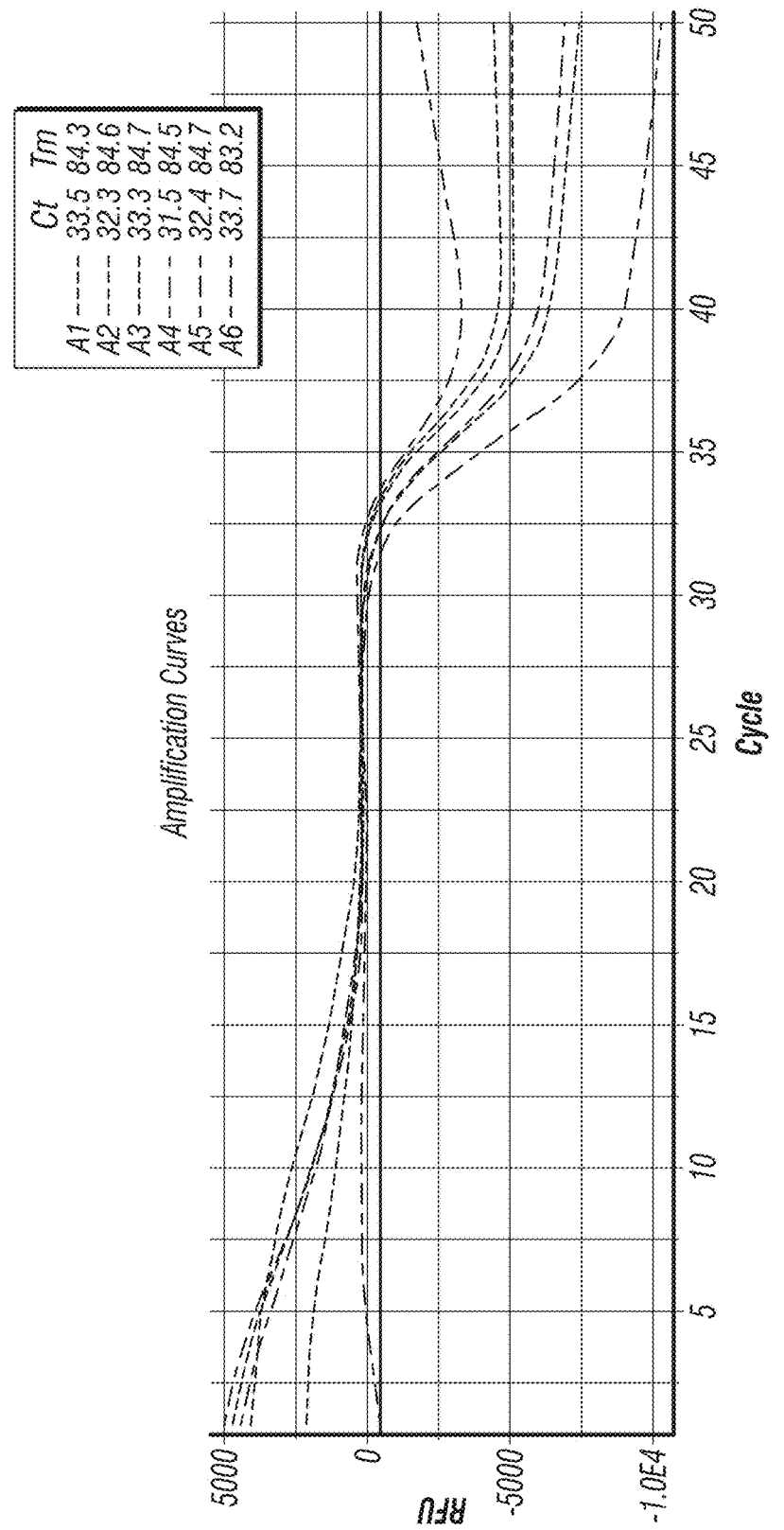
FIG. 4: Graphs show amplification curve and melt curve results for real time PCR amplification of an Influenza A template nucleic acid. Curves were obtained using lyophilized PCR reagent cakes that were covered with melted docosane wax (curves indicted as A1; A2; and A3); or with non-lyophilized ("wet") PCR reagents formulated just prior to PCR cycling (curves indicted as A4; A5; and A6).
Figure 4:
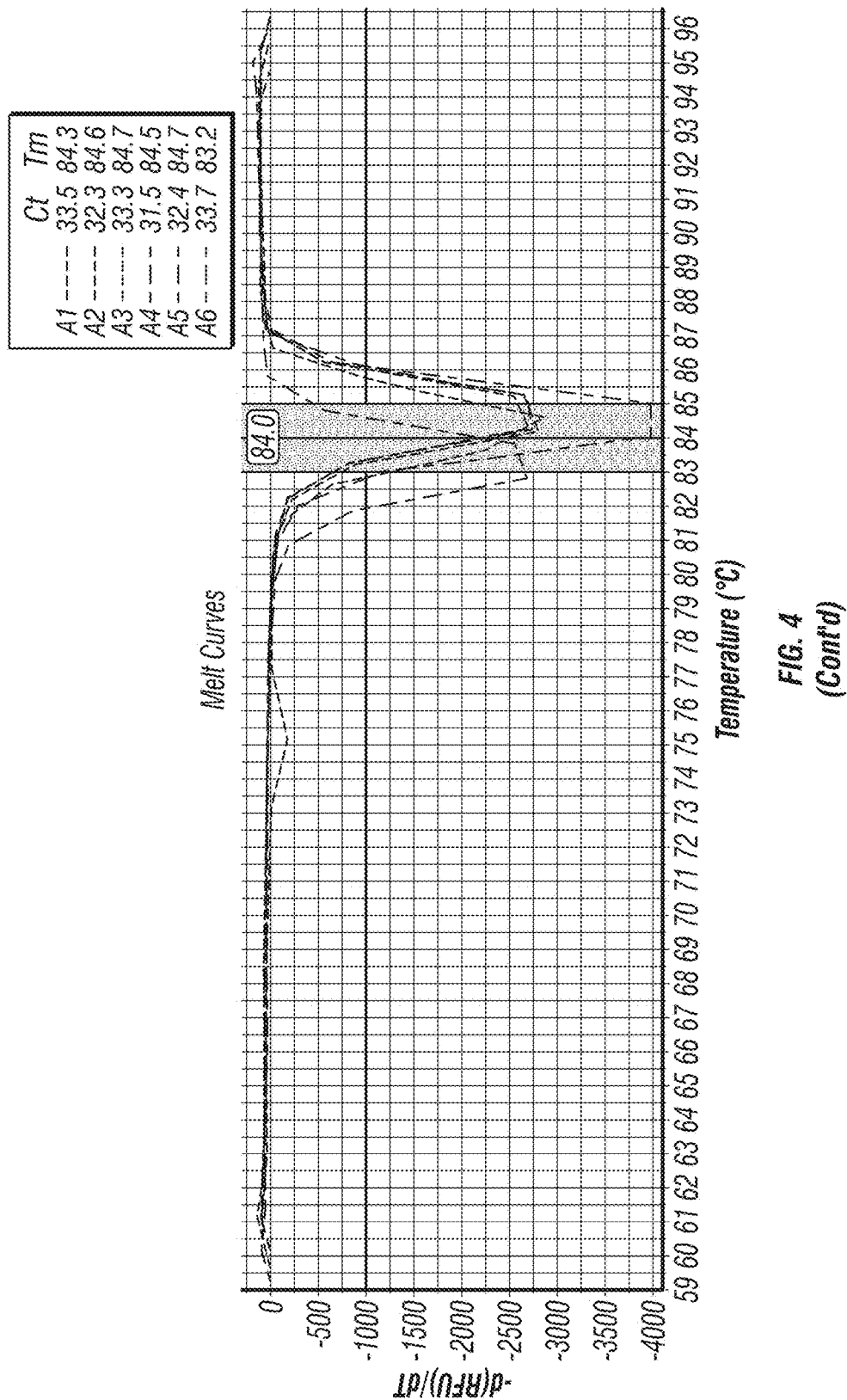
Figure 5A:
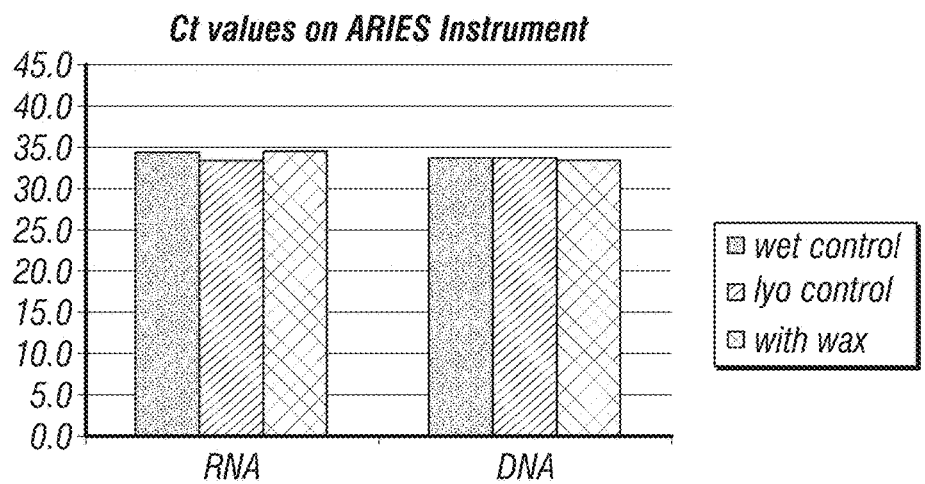
FIG. 5A-D.
Figure 5B:
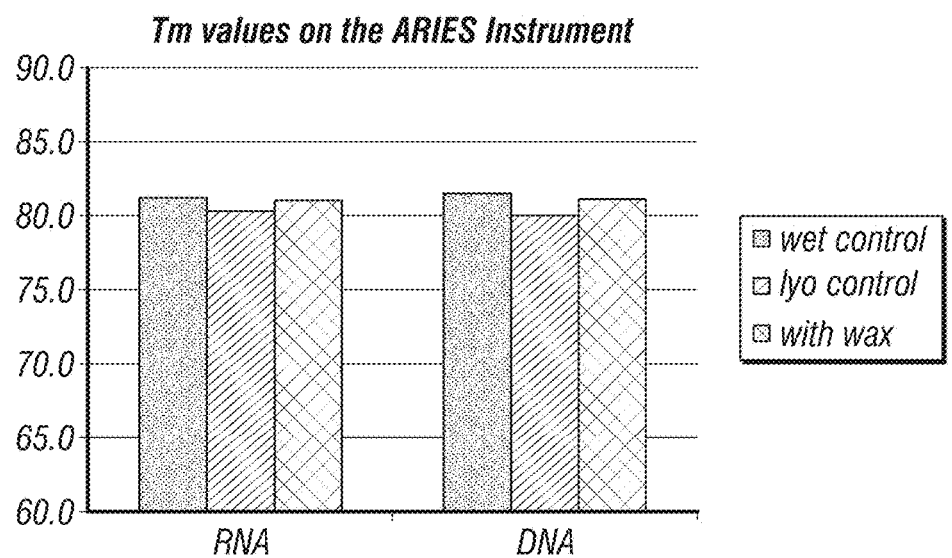
Figure 5C:
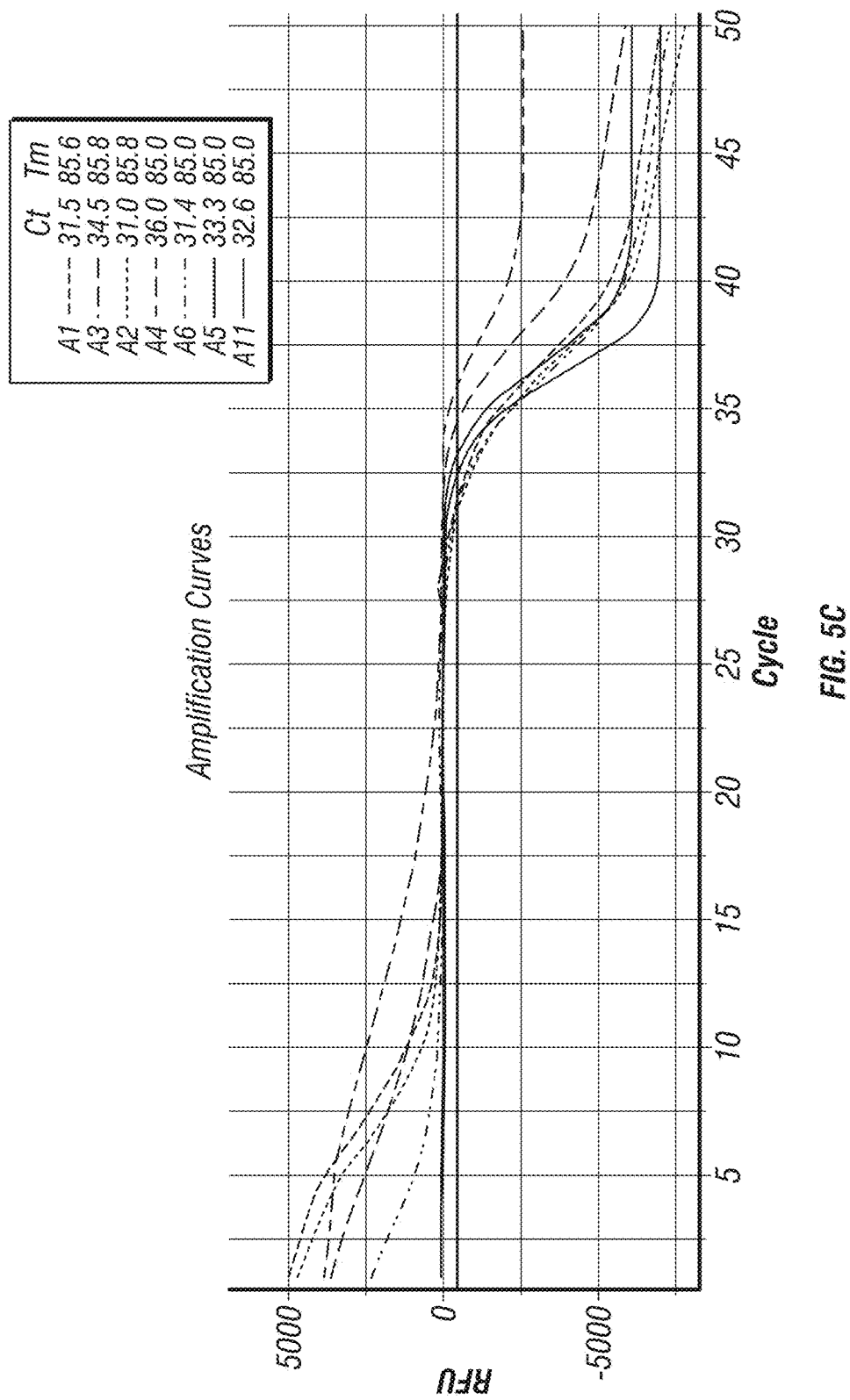
Figure 5C:
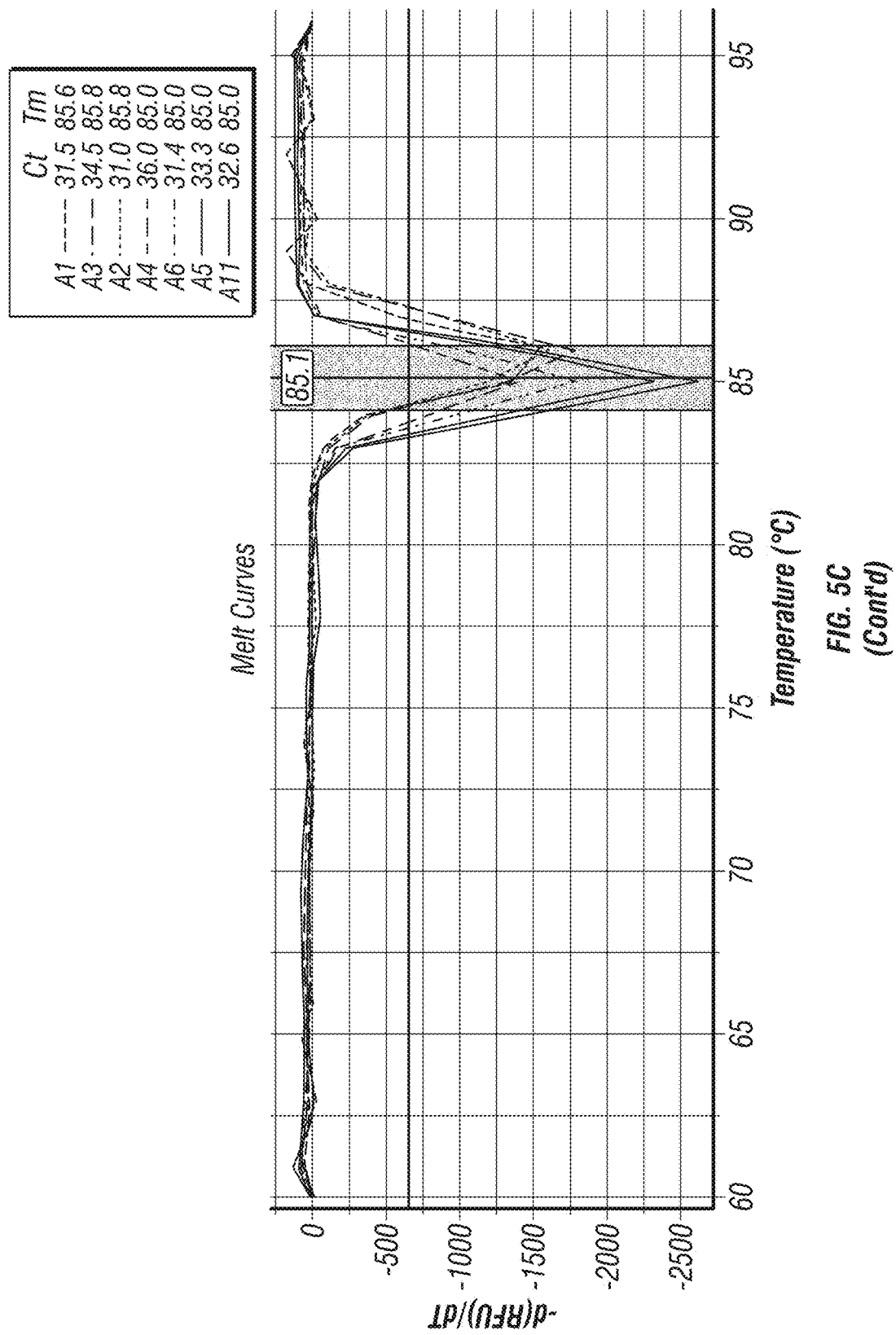
Figure 5D:
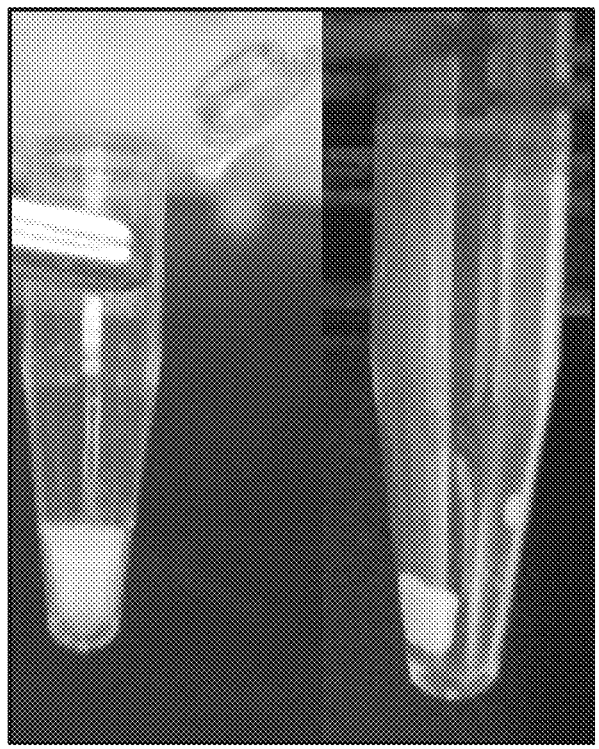

Testing was performed on a real-time thermocycler apparatus and results were compared to a wet control made immediately prior to testing. The wet control contained all of the critical components of the PCR reagent master mix, but did not contain the sugar required for lyophilization. The wax covered lyophilized cakes were heated for 30 seconds and then the Tris buffer was added. The pellet was heated for another 30 seconds and then immediately placed in the thermocycler apparatus for testing. Alternatively, Paraffin wax inversion mixing was done off-instrument on a heat block. The results of the studies comparing the paraffin-coated cake with control are shown below in Table 1 and FIG. 2 (results from amplification using paraffin-coated cakes are labeled as A2-A6 and A8-A12 whereas control is labeled as A1 and A7). These studies demonstrated that quantitative amplification can be successfully achieved using a reagent cake that has been impregnated with paraffin wax.

TABLE 1

Results of PCR with paraffin-coated reagent cakes versus control

|  | average Ct | | Average Tm | |
| --- | --- | --- | --- | --- |
| paraffin | 36.7 | 0.9 | 84.8 | 0.4 |
| Control | 31.7 | 0.4 | 84.8 | 0.3 |

Example 3

Use of Docosane Pellets as Vapor Barrier to the Lyophilized Cake

A 20 μL docosane wax pellet was also added to a 25 μL Influenza A lyophilized cake. The wax was melted on a heat block with an in-well temperature of 50° C. for 3.5 minutes. Testing was performed on a real-time thermocycler apparatus and results were compared to a wet control made immediately prior to testing. The wet control contained all of the critical components of the master mix, but did not contain the sugar required for lyophilization. The results are shown in Table 2 and FIG. 3 (results from amplification using docosane-coated cakes are labeled as A2-A6 and A8-A12 whereas control is labeled as A1 and A7). These studies demonstrated that quantitative amplification can be successfully achieved using a reagent cake that has been coated with docosane wax.

TABLE 2

Results of PCR with docosane-coated reagent cakes versus control

| | average Ct | | Average Tm | |
|---|---|---|---|---|
| docosane | 34.3 | 1.0 | 85.2 | 0.3 |
| Control | 33.5 | 0.8 | 85.0 | 0.5 |

Example 4

Use of Molten Wax (Docosane) as Vapor Barrier to the Lyophilized Cake

Influenza A lyophilized cakes (50 μL cakes) were prepared and coated with 60 μL docosane wax. Docosane wax was heated to 100° C. and then 60 μL was pipetted onto the lyophilized cake and allowed to solidify. Testing was performed on a real-time thermocycler apparatus after melting/inversion mixing of wax-coated cakes, and results were compared to a wet control made immediately prior to testing. The wet control contained all of the critical components of the master mix, but did not contain the sugar required for lyophilization. Results of these studies are shown in FIG. 4 (results from amplification using docosane-coated cakes are labeled as A1-A3 whereas control is labeled as A4-A6). These studies confirmed that quantitative amplification can be successfully achieved using a reagent cake that has been coated with molten docosane wax.

Example 5

RNA and DNA Testing

25 μL lyophilized cakes were prepared using Mouse Hepatitis Virus Primers lyophilized in tubes. Moloney neurine leukemia virus (MMLV) reverse transcriptase enzyme was added to the master mix to allow for detection of both RNA and DNA internal control target using the same lyophilized cakes. Docosane wax (25 μL) was melted over the lyophilized cakes using a heat block with an in-well temperature of 50° C. for 3.5 minutes in 25% relative humidity (RH) conditions. Testing was performed on a real-time thermocycler apparatus with an off-instrument inversion of the wax. To perform the off-instrument inversion, wax covered cakes were heated on a heat block with an in-well temperature of 50° C. for 30 seconds. 50 μL of 50° C. target was added to the tube and the tube was immediately transferred to a thermocycler instrument. The same testing parameters were used for both DNA and RNA. Wax covered lyophilized cakes were compared with the same lyophilized cakes with no wax covering (lyo control) and a wet control. The wet control contained all of the same components as the lyophilized material but was prepared immediately before testing. Results of these studies showed that Ct (Table 3 and FIG. 5A) and Tm (Table 4 and FIG. 5B) values are comparable across all conditions.

TABLE 3

Ct values for DNA and RNA using control reaction versus wax-covered lyophilized pellet

| | wet control | lyo control | with wax |
|---|---|---|---|
| RNA | 34.6 | 33.6 | 34.8 |
| DNA | 33.9 | 33.9 | 33.7 |

TABLE 4

Tm values for DNA and RNA using control reaction versus wax-covered lyophilized pellet

| | wet control | lyo control | with wax |
|---|---|---|---|
| RNA | 81.0 | 80.2 | 81.0 |
| DNA | 81.4 | 80.0 | 81.0 |

Example 6

Wax as a Vapor Barrier and the Quantity of Wax for Use

Influenza A lyophilized cakes (25 μL) were prepared in snap cap tubes. Varying amounts of docosane wax was melted on the lyophilized cakes (20, 15, 10 μL) and allowed to solidify. Wax-covered lyophilized cakes were then placed in a 35° C. oven (a temperature lower than the wax melt temperature to make sure the wax was still solid) containing a pan of water to create a high humidity environment. Material was left in the oven until the uncovered lyo cake control shriveled (~1 hour). Resulting materials were tested on a thermocycler apparatus.

Results of these studies are shown in FIG. 5C-D and indicate that uncovered lyophilized material subjected to high humidity (A4) results in a Ct delay compared to the wet control (A5 and A11) and no-humidity lyophilized control (A6). However, when the material is protected by higher amounts of wax (20 μL and 15 labeled as A1 and A2, respectively), Ct values are comparable to the controls, even after exposure to high humidity. Reduced levels of wax component (10 μL, A3) also resulted in a Ct delay when subjected to high humidity.

Example 7

Ball on Top of the Lyo Cake Aids in Wax Inversion

25 μL Mouse Hepatitis Virus specific primer reaction mix contained in lyophilized cakes were prepared and covered with 25 μL docosane wax in a vacuum oven set to 55° C. for 15 minutes. A ceramic ball was placed on top of the wax covered cake prior to melting, which resulted in the ceramic ball being embedded in the wax after melting and re-solidifying. Testing was performed in-tube using Mouse Hepatitis Virus RNA as target. Wax inversion occurred during the wax melting of the RT step and was aided by the ceramic ball. The ceramic ball dropped to the bottom through gravity during the wax melting procedure, thus breaking the surface tension and the interface between the wax and the resuspension buffer, allowing any "stuck" wax to rise to the top. The ceramic ball also freed any air bubbles already stuck in the resuspension buffer and allowed for a break in the surface tension at the bottom of the tube, preventing air bubbles from forming or remaining near the bottom.

Figure 6A:
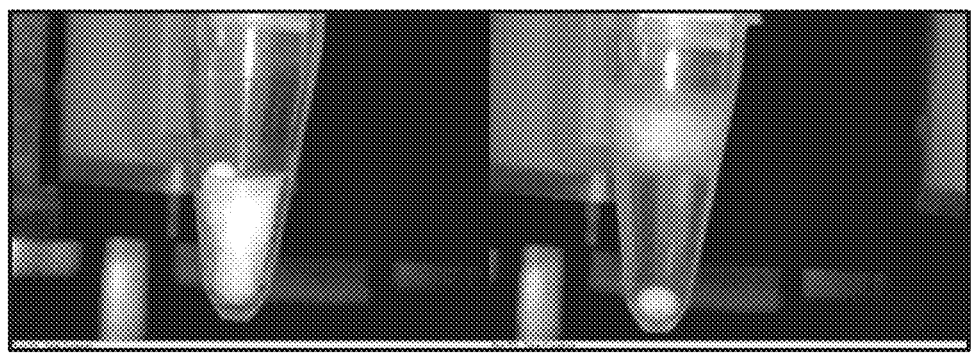
FIG. 6A-B.
Figure 6B:
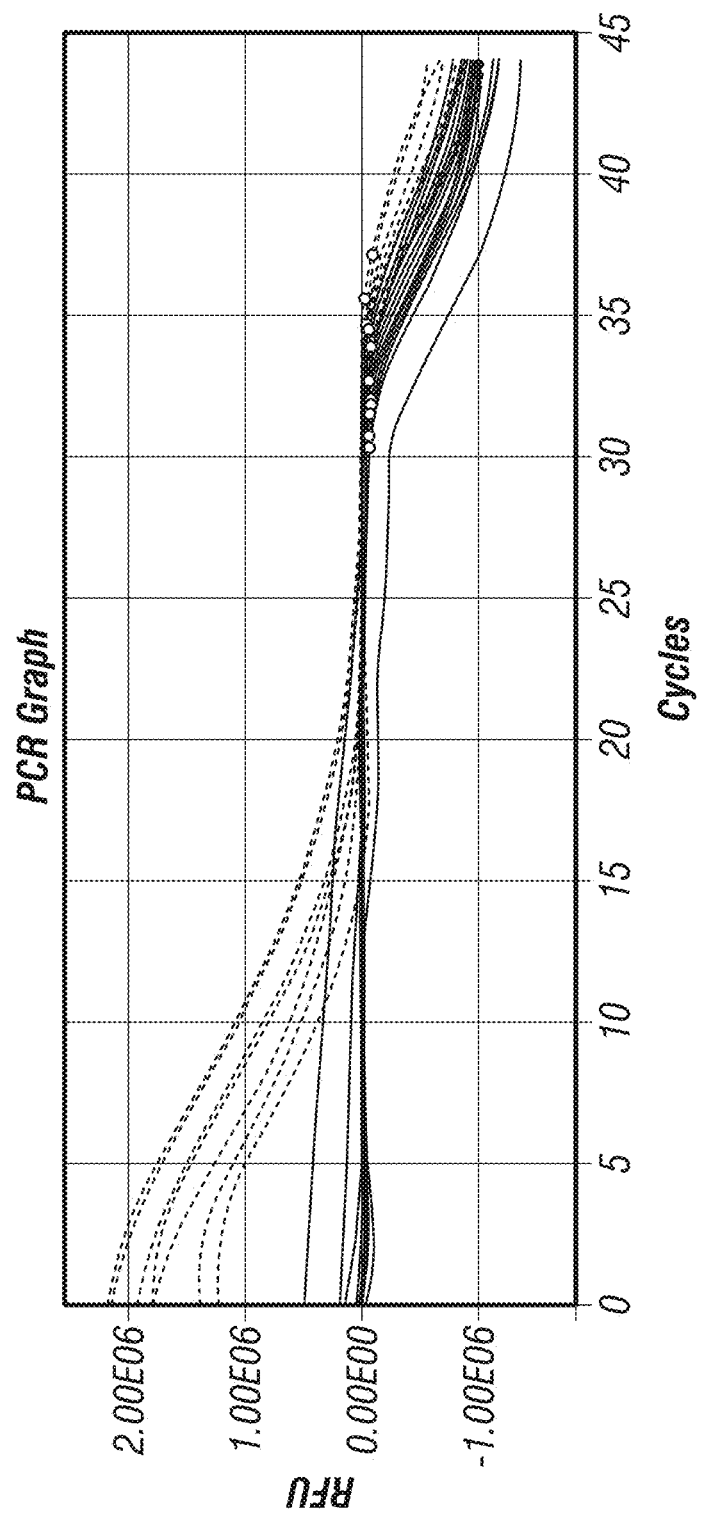
Figure 6B:
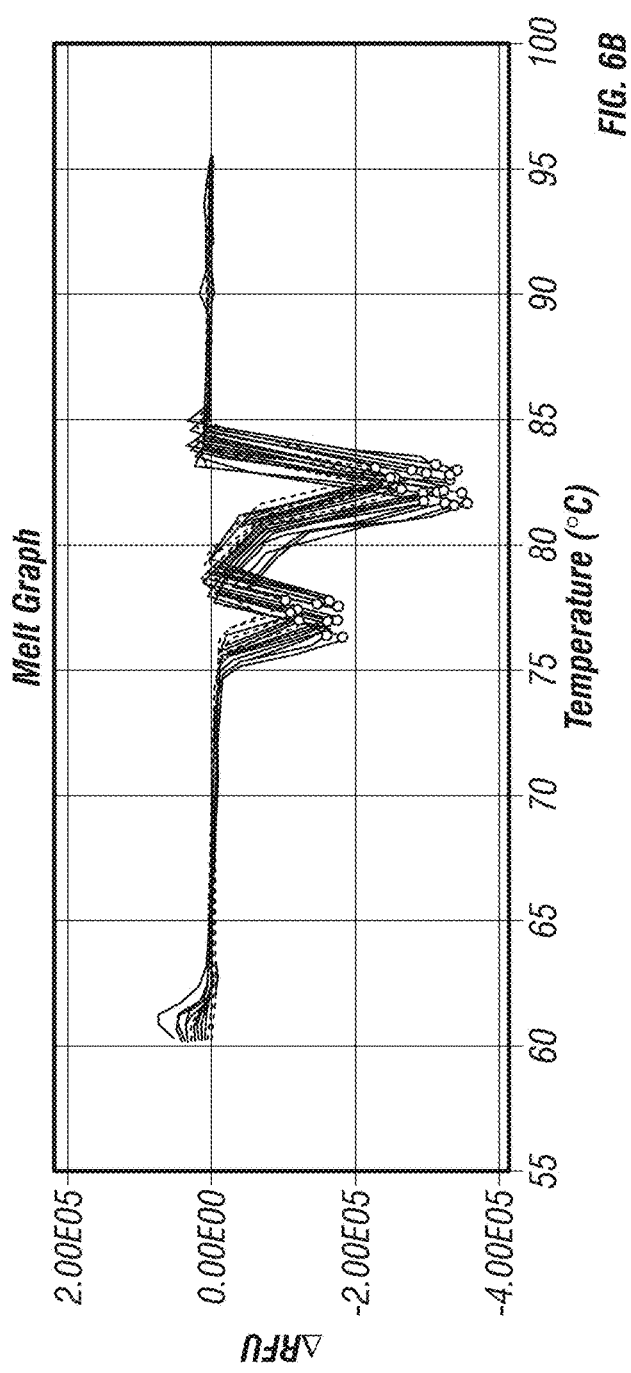

Testing was compared to a wet control that was prepared immediately before testing. While this wet control contained all of the critical components of master mix, it did not contain the dextran and trehalose used for lyophilization. Results of the studies shown in FIG. 6A-B (ceramic ball wax-coated reagent cake is indicated in dashed lines; wet control indicated in solid lines) and Table 5 indicates that wax covered lyophilized material with a ceramic ball on top resulted in 100% detection of the target in both the amplification and melt.

TABLE 5

Real-time PCR with ceramic ball wax-coated reagent cake versus wet control

| Condition | Ct | STDEV |
|---|---|---|
| wet control | 31.87 | 0.94 |
| Ceramic | 34.94 | 1.14 |

Example 8

Lyophilized Cake with Steel Sphere on Bottom of Cake and Mixing Processes

A chrome steel magnetic ball was added to the PCR tubes and 25 μL of PCR reagent master mix (specific for Norovirus amplification) was added on top of the ball for lyophilization. The magnetic ball is therefore positioned underneath the cake and no additional ball(s) were added post-wax addition. A subset of the Norovirus cakes were covered with 25 of docosane wax. Wax was added as a pellet and then melted in a vacuum oven set to 50° C. for 5 minutes. Testing was performed on a thermocycler apparatus with a mixing step during the Reverse Transcriptase (RT) step.

Reconstitution of the Lyophilized Master Mix was initiated 90 seconds after the start of the reverse transcriptase step, and after the wax inversion. Magnetic mixing using the metal ball aids in the inversion of wax that has not naturally inverted by disrupting the surface tension at the wax-resuspension buffer interface. The metal ball also reduces the surface tension, which allows for any air bubbles that may be caught in the resuspension buffer to be released and rise to the top. Finally, the magnetic mixing is used to mix the resuspension buffer with the lyophilized cake and ensure uniform distribution of master mix components. During the mixing process, a magnet was moved towards the PCR tube, which lifted the metal ball to just under the liquid/wax interface, where it was held for 3 seconds. The magnet then moved away and waited for 3 seconds, thereby releasing the ball to the bottom. This continued for 90 seconds.

Testing of the wax covered lyophilized pellet with the metal ball was compared to a "wet" master mix that was prepared immediately before testing and contained all of the same components as the master mix; however, it used a mineral oil vapor barrier instead of a wax vapor barrier. Results were also compared to the same lyophilized reagent cakes that had been wax covered, but not mixed and that had not been covered with wax and had been either unmixed, hand mixed, or magnetic mixed.

Figure 7A:
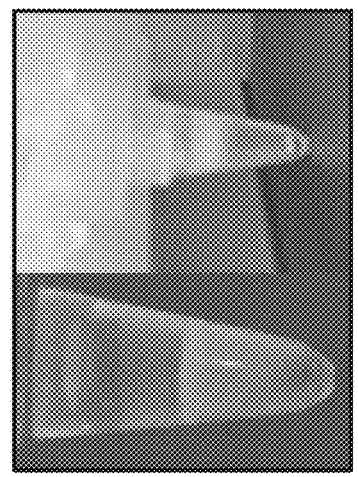
FIG. 7A-B.
Figure 7B:
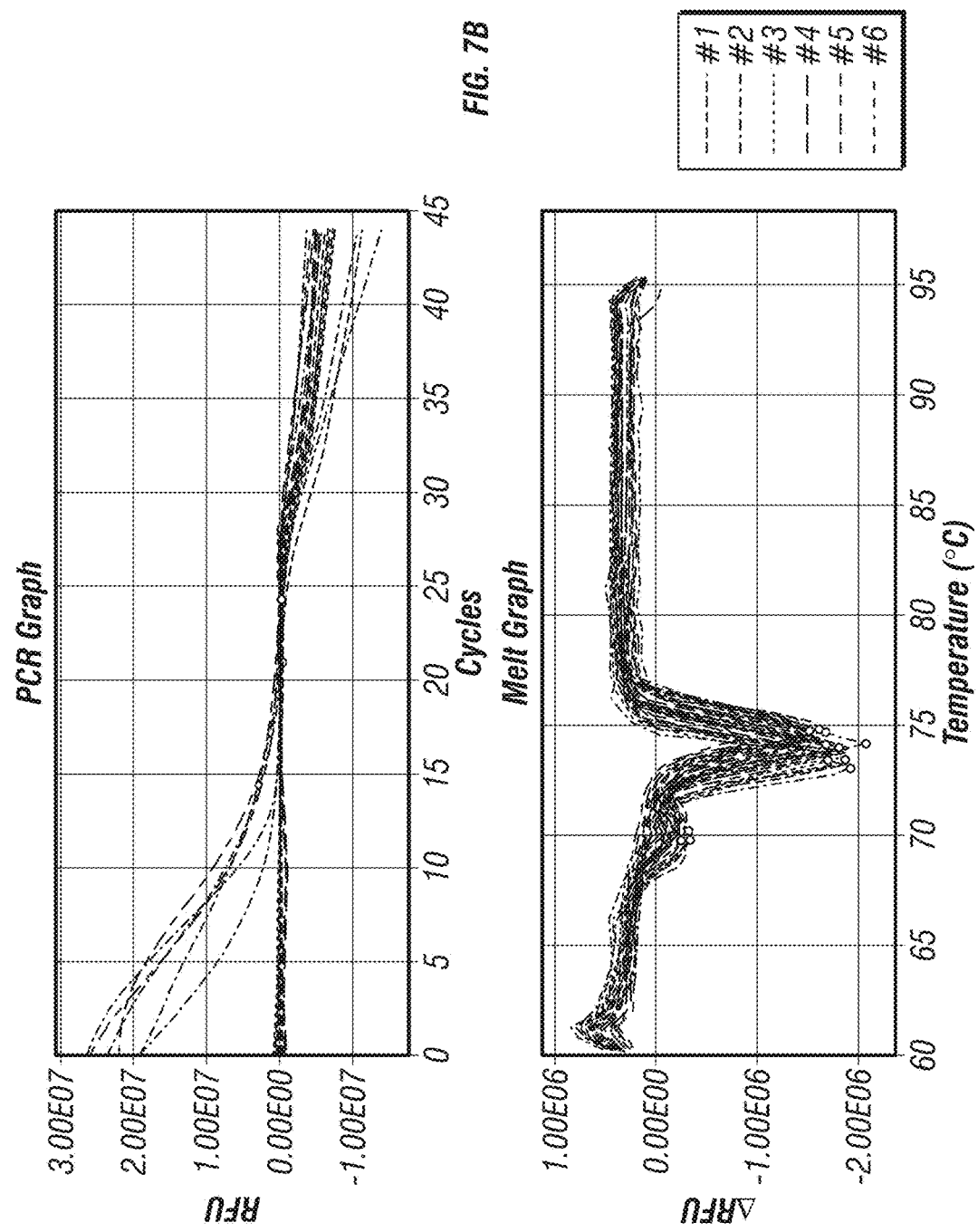
Figure 7B:
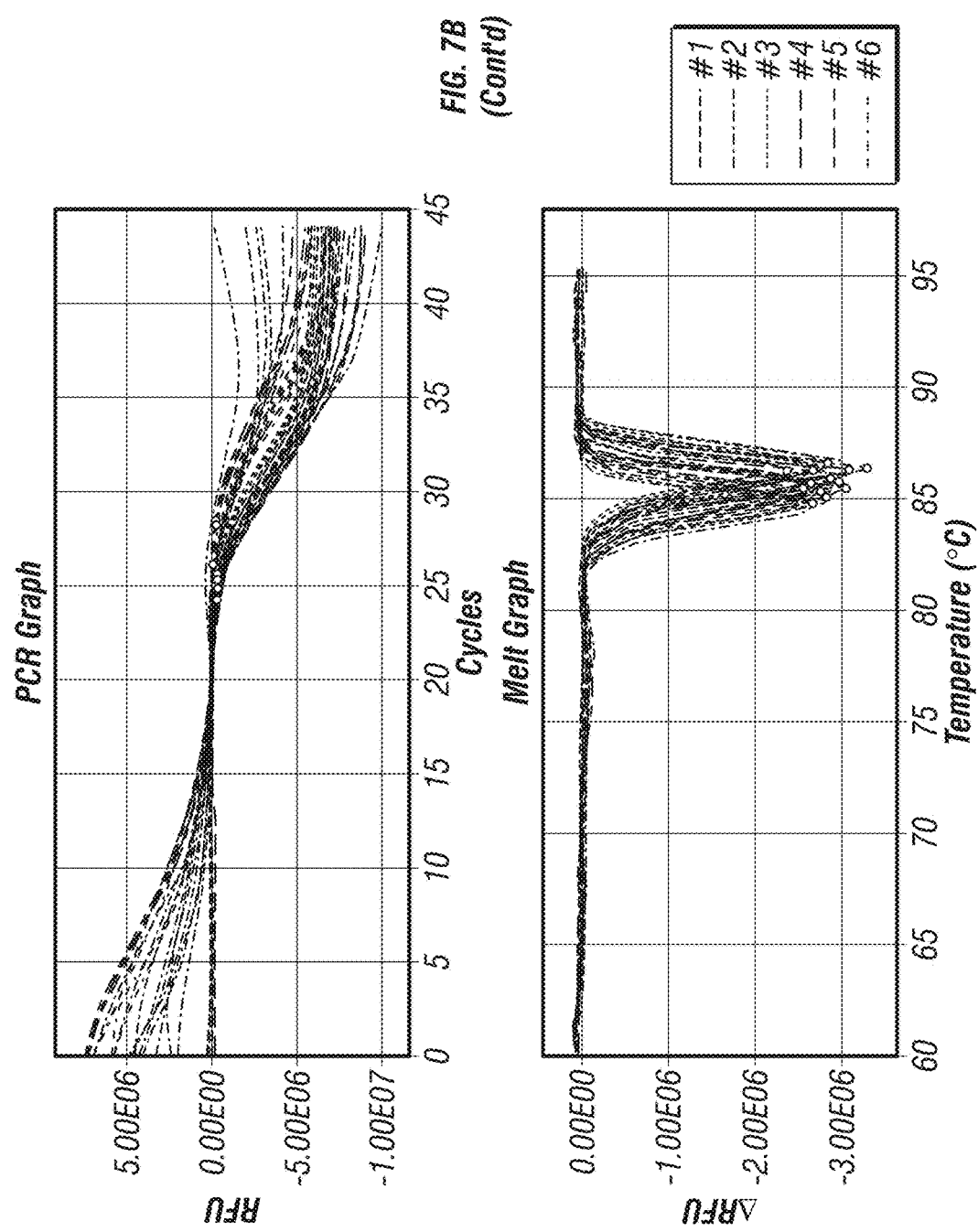
Figure 7B:
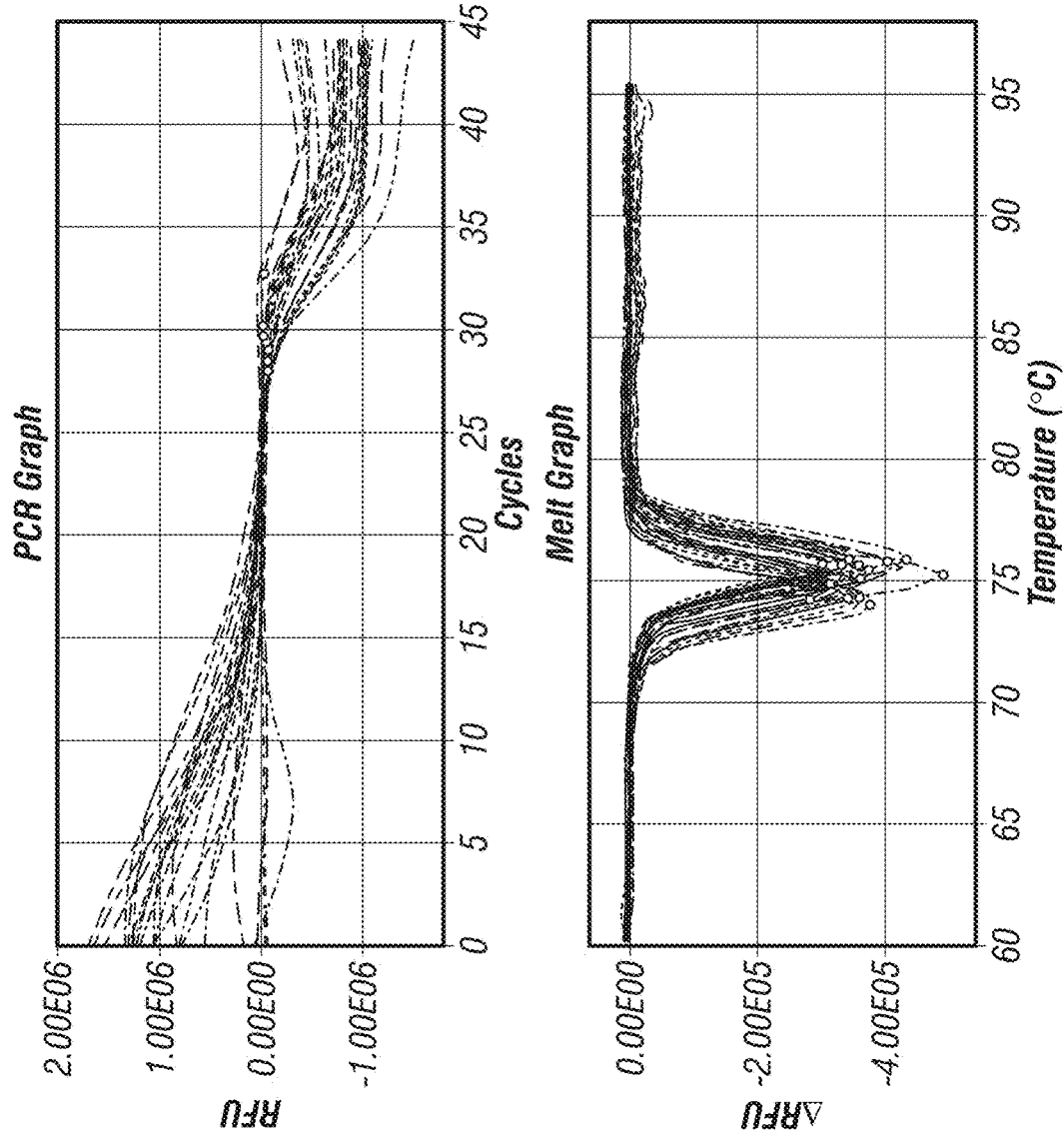

Results of the studies are shown in FIG. 7B and Table 6. These results demonstrated that lack of mixing (curves labeled #2 and #5) resulted in significant fluorescence spike/noise at the beginning of cycling ("doglegs"), which may affect detection of amplification (as exemplified by the curves labeled #5 in the FAM channel). 100% detection of Norovirus was achieved in the wax covered lyophilized material with the magnetic stainless steel ball on the bottom of the lyophilized cake.

TABLE 6

Real-time RT-PCR results from amplification of Norovirus target using different lyophilized reagent cakes and mixing conditions.

| | Norovirus | | | | | |
|---|---|---|---|---|---|---|
| | FAM | | AP559 | | AP593 | |
| | Mean Ct | Stdev Ct | Mean Ct | Stdev Ct | Mean Ct | Stdev Ct |
| Wet Hand Mixed w/ Ball | 25.38 | 0.77 | 28.67 | 0.42 | 25.3 | 0.22 |
| Uncovered Lyo Unmixed | 25.55 | 0.69 | 29.01 | 0.65 | 25.45 | 0.46 |
| Uncovered Lyo pipette Mixed w/ Ball | 25.45 | 0.53 | 27.64 | 0.14 | 25.52 | 0.17 |
| Uncovered Lyo Magnetic Mixed | 26.18 | 0.95 | 29.05 | 0.35 | 24.93 | 0.49 |
| Wax Sealed Lyo w/ Ball No Mix | n/a | n/a | 31.06 | 0.75 | 27.99 | 0.37 |
| Wax Sealed Lyo Magnetic Mixed | 27.70 | 0.52 | 30.65 | 0.47 | 27.94 | 0.46 |

Example 9

Comparison of Ceramic Vs Metal Spheres for Mixing Process

Lyophilized reagent cakes specific for HSV detection (25 μL) were prepared and covered with 25 μL of docosane wax. Wax was added as a pellet and then melted in a vacuum oven set to 50° C. for 5 minutes. After solidification, a ceramic ball or a metal ball was placed on top of the cakes. PCR was performed on a thermocycler apparatus with a mixing step during the Reverse Transcriptase (RT) step. The mixing step began 90 seconds after the start of the RT step, which allowed for wax inversion to occur. During the wax melting process, the metal ball placed on top dropped to the bottom via gravity. Once it was at the bottom, a magnet moved towards the PCR tube, which lifted the metal ball to just under the liquid/wax interface, where it was held for 3 seconds. The magnet then moved away and waited for 3 seconds, thereby releasing the ball to the bottom. This continued for 90 seconds. The ceramic ball was also placed on top and dropped to the bottom through gravity during the wax melting procedure, but since the material is not magnetic, it undergoes no further mixing. Testing was compared to a "wet" master mix that was prepared immediately before testing and contained all of the same components as the master mix; however, it used a mineral oil vapor barrier instead of a wax vapor barrier.

Figure 8:
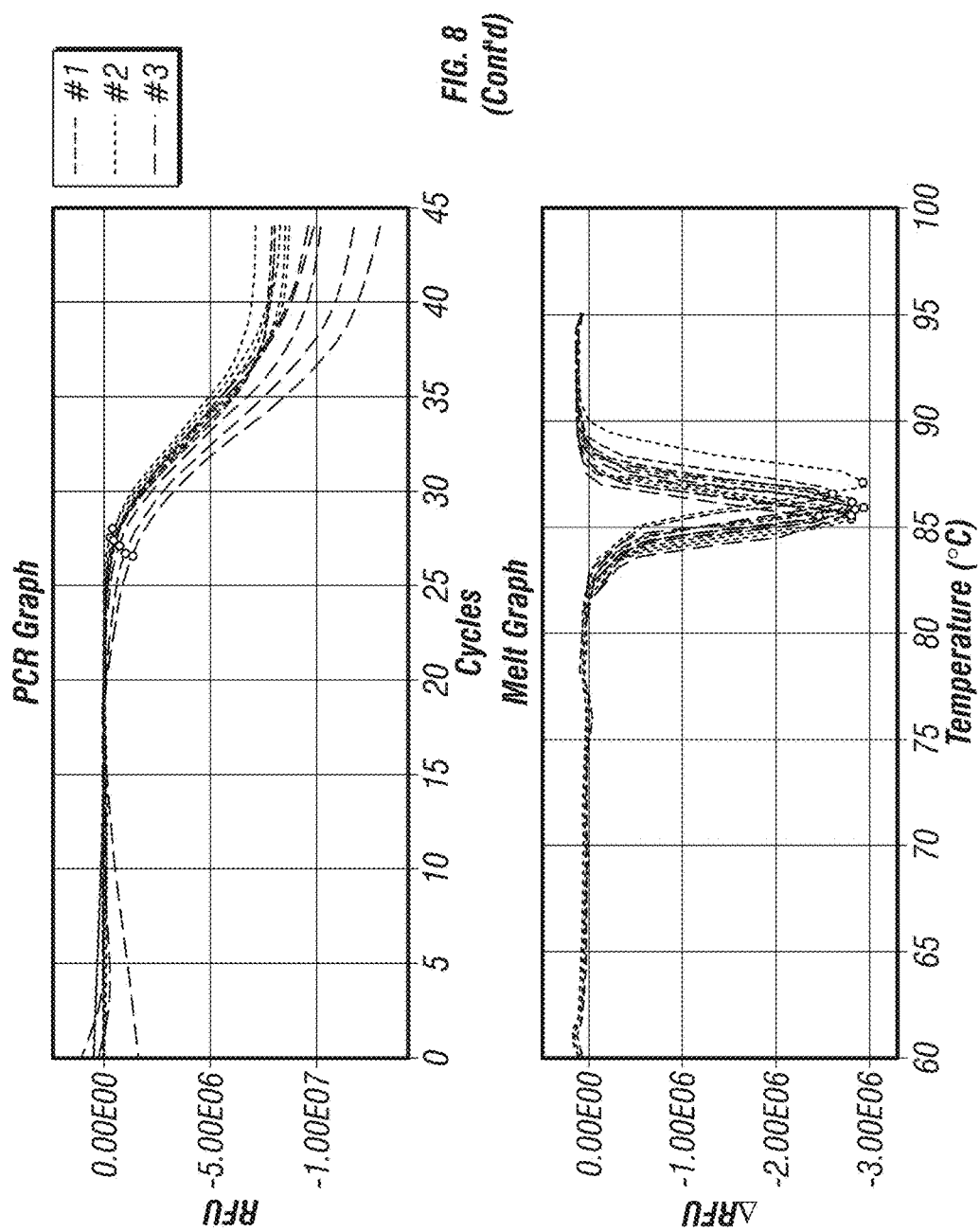
FIG. 8: Graphs show amplification curve (left panels) and melt curve (right panels) results for real time PCR amplification of HSV template nucleic acid. The results show curves obtained using (1) non-lyophilized ("wet") PCR reagents that were not mixed (depicted as curve #1); (2) lyophilized PCR reagent cakes covered with melted docosane wax and including a ceramic ball that was not mixed (depicted as curve #2); and (3) lyophilized PCR reagent cakes covered with melted docosane wax and including a stainless steel ball that were magnetically mixed (depicted as curve #3).

Results of these studies are shown in Table 7 and FIG. 8 (Curves labeled #2 indicates mixing with a stainless steel ball; #3 indicates reactions with the ceramic ball; and #1 indicated the "wet" reagent control). Results of these studies show that there is no significant functional difference between wet, ceramic, and the metal ball conditions in terms of calculated Ct and Tm values. However, the addition of the mixing with the stainless steel ball resulted in a decrease in "doglegs" or generation of a flatter fluorescence base-line when compared to the ceramic, which is likely the effect of increased mixing.

TABLE 7

Tm and Ct results for reactions using different mixing conditions and different ball compositions.

| | HSV-FAM Average Ct | | HSV-FAM Average Tm | | DNA Control-AP559 average Ct | | DNA Control AP559 Average Tm | |
|---|---|---|---|---|---|---|---|---|
| wet | 27.19 | 0.02 | 85.75 | 0.13 | 34.25 | 0.71 | 73.57 | 0.18 |
| Ceramic | 27.14 | 0.62 | 86.02 | 0.24 | 32.86 | 0.69 | 72.69 | 0.59 |
| Metal Ball | 27.41 | 0.06 | 85.98 | 0.15 | 32.95 | 0.37 | 72.93 | 0.72 |

Example 10

Wax Formulations and Formulation Methods

Further wax compositions were formulated for use in making stabilized lyophilized reagent cakes. In a first example protocol, a wax containing 30% docosane and 70% PDMS oil was formulated. First, a 1.5 mL tube of 100% docosane wax was heated at 65° C. using a thermocycler. 700 µL PDMS oil was added to a new 1.5 mL tube and also heated to 65° C. 300 µL of the melted 100% docosane wax was then added to the 700 µL of PDMS in the 1.5 mL vial. The mixture continued to be heated at 65° C. and mixed by aspiration/dispense with a P1000 pipette. Once the wax composition was thoroughly mixed, 25 µL aliquots of the wax mixture were pelleted onto a foil covered cold block. Pellets were allowed to cool and formed solid wax within a minute. Pelleting was repeated until the desired number of pellets was produced. The pellets may be further melted or deposited as a solid for use in coating lyophilized reagent cakes.

A further wax formulation was composed and contained 15% docosane, 15% paraffin and 70% PDMS oil. For this formulation 100% docosane wax was melted at 65° C. in a 1.5 mL tube. Likewise, 100% paraffin wax was melted at 65° C. in a 1.5 mL tube. Next, 500 µL of 100% docosane wax was added to 500 µL of 100% paraffin in a new 1.5 mL vial. The mix continued to be heated at 65° C. and was mixed by aspiration/dispense with a P1000 pipette. Separately, 700 µL PDMS oil was added to another new 1.5 mL tube and heated to 65° C. Next, 300 µL of the docosane/paraffin mixture was added to the 700 µL PDMS in the new 1.5 mL vial. The final wax mixture continued to be heated at 65° C. and mixed by aspiration/dispense with a P1000 pipette. Once thoroughly mixed, 25 µL aliquots of the wax mixture were pelleted onto a foil covered cold block. Resulting pellets were cooled and formed solid wax within a minute. Pelleting was repeated until the desired number of pellets was produced. The pellets may be further melted or deposited as a solid for use in coating lyophilized reagent cakes.

Example 11

Use of a Two-Layered Wax as Vapor Barrier to the Lyophilized Cake

Figure 9A:
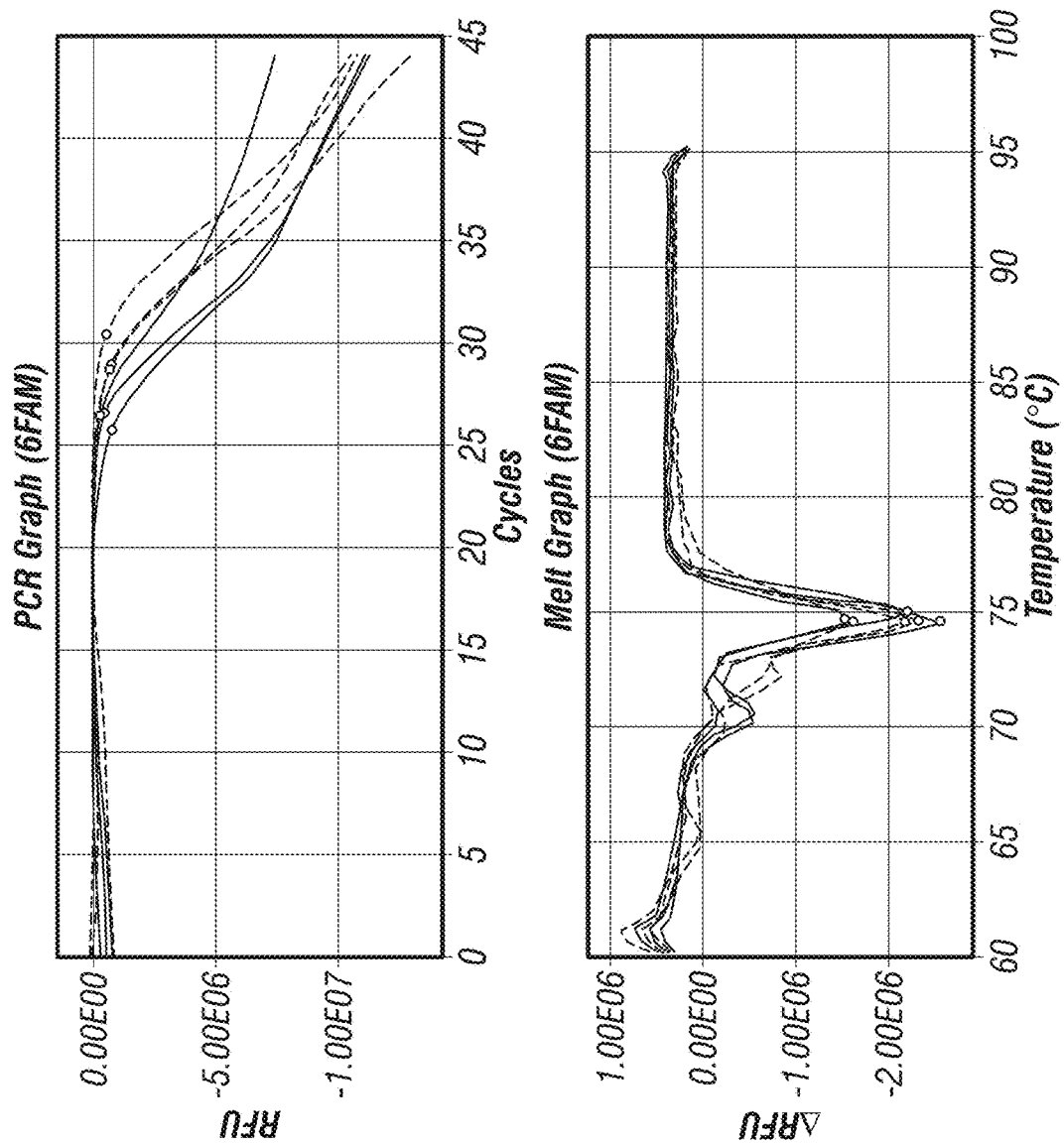
FIG. 9A-C.
Figure 9B:
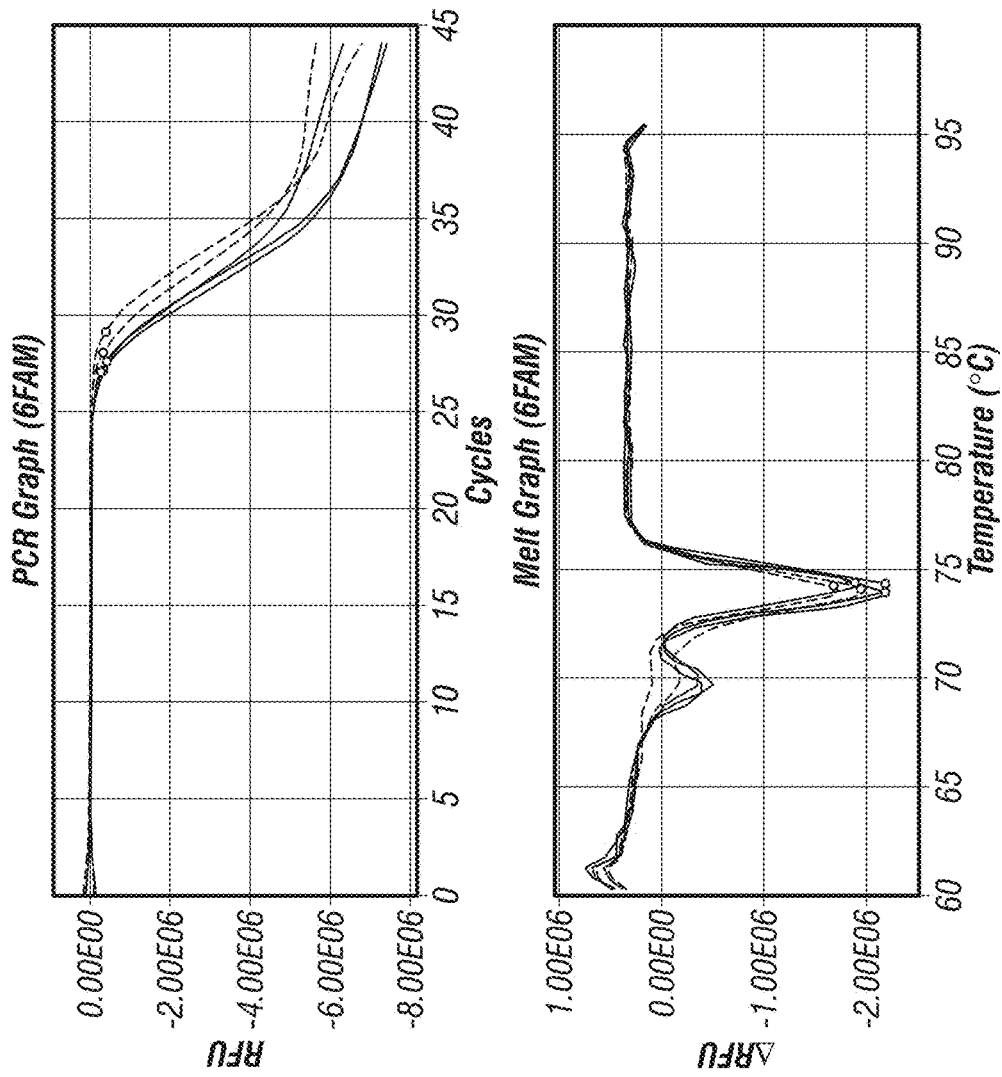
Figure 9C:
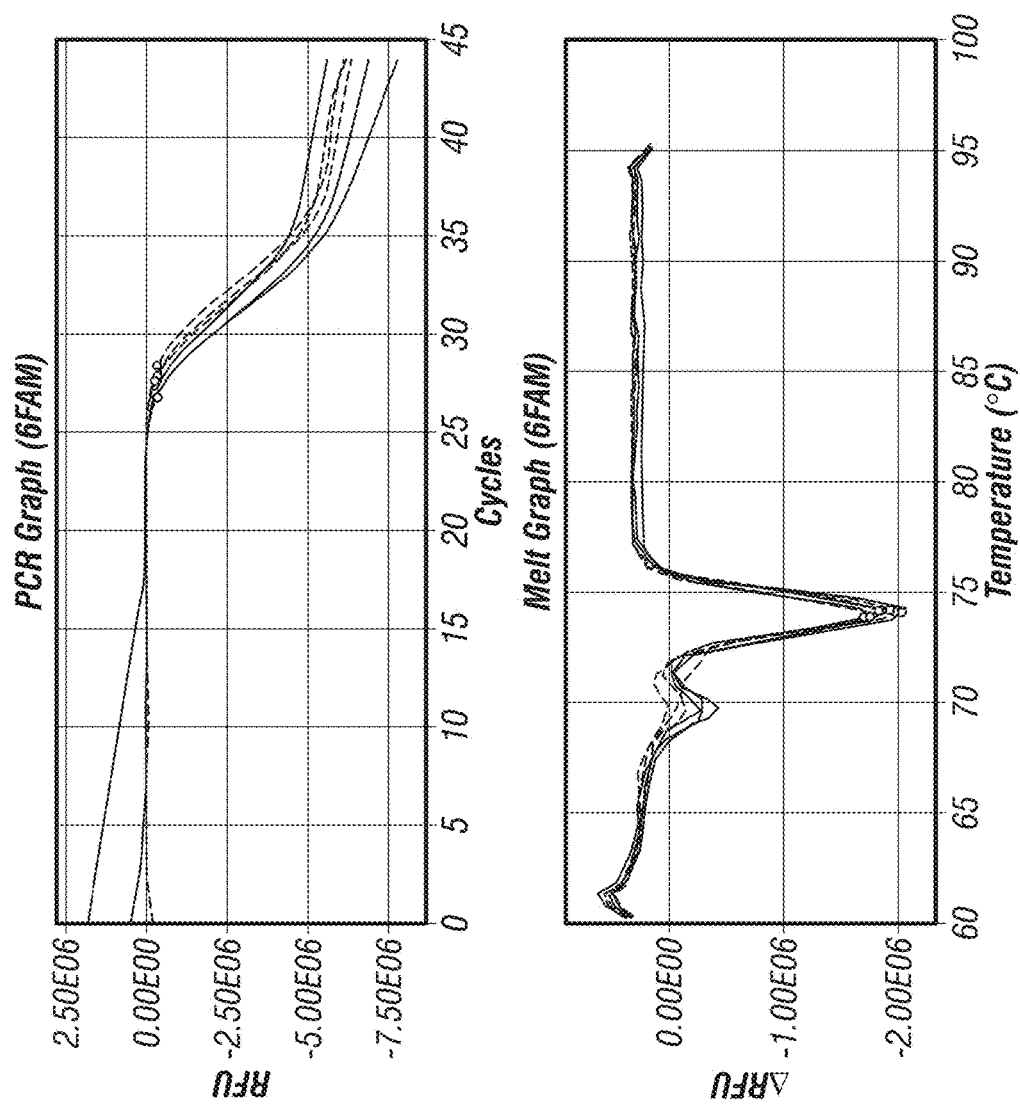

Lyophilized reagent cakes (25 µL) were prepared in snap cap tubes that comprise real-time PCR reagents and primers for Norovirus RNA amplification. The lyophilized PCR reagent cake was overlaid with 25 µL docosane wax or docosane wax overlay followed by 15 µL of Chill Out™ wax or docosane wax overlay followed by 15 µL of mineral oil. The docosane wax cakes and the two-layered wax cakes were stored in a 80% Relative Humidity chamber or in a sealed, dry chamber (control) for 3 days. Testing was performed on a real-time thermocycler apparatus and results were compared to the control. The results are shown in FIG. 9. Results show that the docosane, or docosane overlaid with chill out wax or docosane overlaid with mineral oil provides an effective vapor barrier.

Example 12

Use of Combination of Waxes as Vapor Barriers to the Lyophilized Cake

Figure 10:
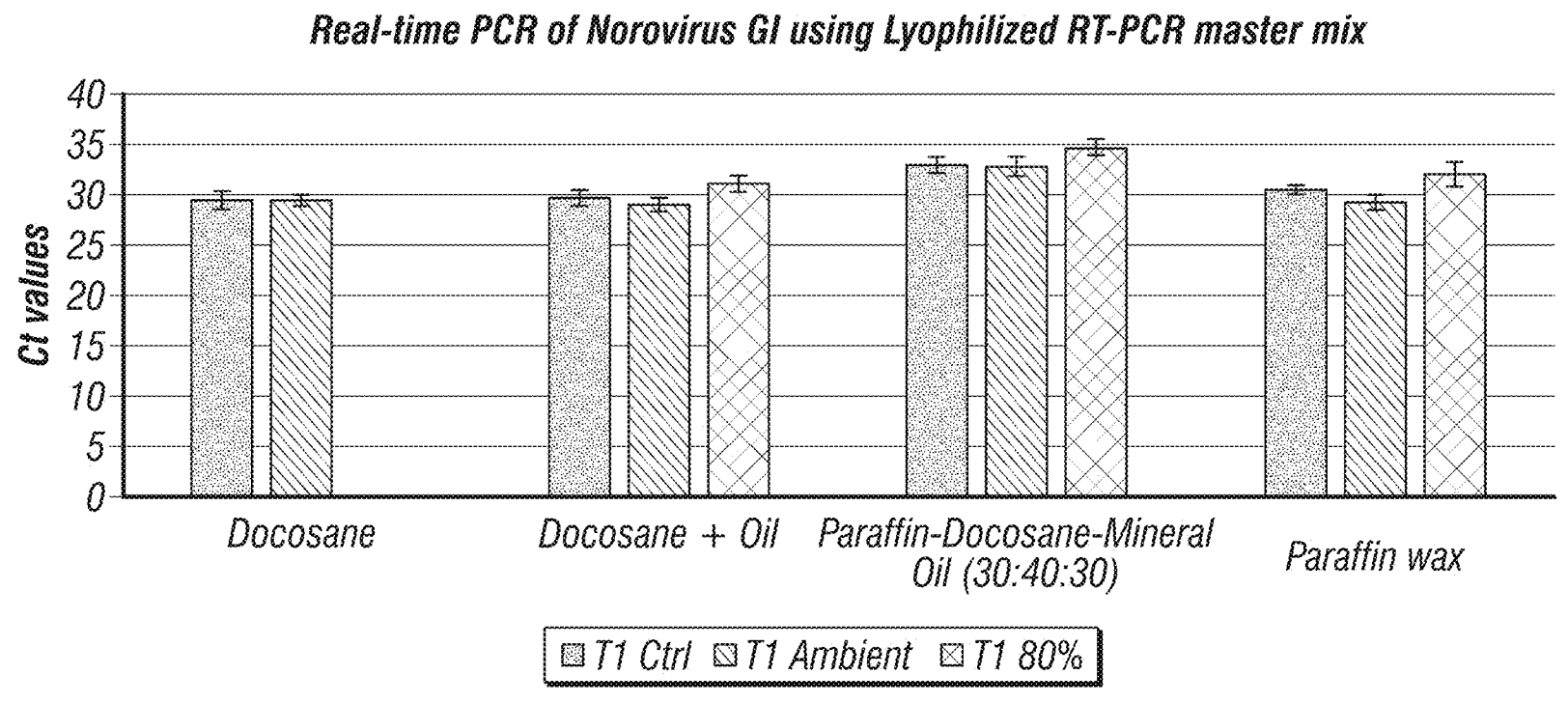

Lyophilized reagent cakes (25 µL) were prepared in snap cap tubes that comprise real-time PCR reagents and primers for Norovirus RNA amplification. The lyophilized PCR reagent cake was overlaid with 30 µL docosane wax or docosane wax overlay followed by 15 µL of mineral oil or the lyophilized PCR reagent cake was overlaid with a 30 µL blend of waxes (Paraffin wax:Docosane wax:mineral oil in the ratio of 30:40:30, volume:volume:volume) or lyophilized PCR reagent cake overlaid with 30 µL Paraffin wax. The docosane wax cakes and the wax-layered lyophilized cakes were stored in a dry box (T1 CTRL), or stored in a ambient environment (T1 Ambient) or stored in a 80% Relative Humidity chamber (T1 80%) for 1 month. Testing was performed on a real-time thermocycler apparatus and results were compared to the control (T1 CTRL). The results are shown in FIG. 10. Results show that a combination of waxes provided a more effective vapor barrier.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,432,272
U.S. Pat. No. 5,965,364
U.S. Pat. No. 6,001,983
U.S. Pat. No. 6,037,120
U.S. Pat. No. 6,140,496
U.S. Pat. No. 6,977,161
U.S. Pat. No. 7,422,850
Crowe, et al. *Biochem. J.* 242: 1-10 (1987).
"The trehalose myth revisited: Introduction to a symposium on stabilization of cells in the dry state", Cryobiology 43, 89-105 (2001).
McMinn et al., *J. Am. Chem. Soc.* 1999, 121:11585
Ren, et al., *J. Am. Chem. Soc.* 1996, 118:1671

What is claimed is:

1. A method of performing PCR comprising:
   (a) obtaining a receptacle containing a wax-treated lyophilized pellet comprising a DNA polymerase and a sugar, wherein the wax-treated lyophilized pellet is formed by heating the lyophilized pellet to at least 50° C. in the presence of a wax, then solidifying the wax;
   (b) adding an aqueous liquid comprising nucleic acids on top of the wax-treated lyophilized pellet;
   (c) melting the wax and inverting the wax and the aqueous liquid in the receptacle to form a wax layer and a reaction solution layer in the receptacle; and
   (d) performing at least one cycle of PCR.

2. The method of claim 1, further comprising mixing the reaction solution layer.

3. The method of claim 2, wherein the receptacle further contains a magnetically responsive solid object and mixing the reaction solution layer comprises inducing movement of the magnetically responsive solid object with a magnet.

4. The method of claim 1, wherein the sugar is trehalose, dextran, mannitol, sucrose, raffinose, or a combination thereof.

5. The method of claim 1, wherein the wax is a first wax and the receptacle further contains a second wax.

6. The method of claim 5, wherein the first wax is liquid at room temperature and the second wax is solid at room temperature.

7. The method of claim 1, wherein the wax has a melting temperature that is between 25° C. and 50° C.

8. The method of claim 1, wherein the wax is a petroleum wax.

9. A method of performing RT-PCR comprising:
   (a) obtaining a receptacle containing a wax-treated lyophilized pellet comprising a RNA polymerase, a DNA polymerase, and a sugar, wherein the wax-treated lyophilized pellet is formed by heating the lyophilized pellet to at least 50° C. in the presence of a wax, then solidifying the wax;
   (b) adding an aqueous liquid comprising nucleic acids on top of the wax-treated lyophilized pellet;
   (c) melting the wax and inverting the wax and the aqueous liquid in the receptacle to form a wax layer and a reaction solution layer in the receptacle;
   (d) performing a reverse transcription reaction; and
   (e) performing at least one cycle of PCR.

10. The method of claim 9, further comprising mixing the reaction solution layer.

11. The method of claim 10, wherein the receptacle further contains a magnetically responsive solid object and mixing the reaction solution layer comprises inducing movement of the magnetically responsive solid object with a magnet.

12. The method of claim 9, wherein the sugar is trehalose, dextran, mannitol, sucrose, raffinose, or a combination thereof.

13. The method of claim 9, wherein the wax is a first wax and the receptacle further contains a second wax.

14. The method of claim 13, wherein the first wax is liquid at room temperature and the second wax is solid at room temperature.

15. The method of claim 9, wherein the wax has a melting temperature that is between 25° C. and 50° C.

16. The method of claim 1, wherein the wax-treated lyophilized pellet further comprises a ceramic ball, glass ball, magnetic ball, or metal ball.

17. The method of claim 9, wherein the lyophilized pellet further comprises a ceramic ball, glass ball, magnetic ball, or metal ball.

18. The method of claim 1, wherein the wax-treated lyophilized pellet is formed by heating the lyophilized pellet to at least 50° C. in the presence of a solid wax pellet.

19. The method of claim 1, wherein the wax-treated lyophilized pellet is formed by heating the lyophilized pellet to at least 50° C. in the presence of a liquid wax.

20. The method of claim 9, wherein the wax-treated lyophilized pellet is formed by heating the lyophilized pellet to at least 50° C. in the presence of a solid wax pellet.

21. The method of claim 9, wherein the wax-treated lyophilized pellet is formed by heating the lyophilized pellet to at least 50° C. in the presence of a liquid wax.

* * * * *